United States Patent [19]
Junge et al.

[11] 4,260,622
[45] Apr. 7, 1981

[54] ANIMAL FEEDSTUFFS EMPLOYING 3,4,5-TRIHYDROXYPIPERIDINES

[75] Inventors: Bodo Junge; Hans P. Krause; Lutz Müller; Walter Puls, all of Wuppertal, Fed. Rep. of Germany

[73] Assignee: Bayer Aktiengesellschaft, Leverkusen, Fed. Rep. of Germany

[21] Appl. No.: 77,507

[22] Filed: Sep. 20, 1979

Related U.S. Application Data
[62] Division of Ser. No. 936,280, Aug. 23, 1978.

[30] Foreign Application Priority Data
Aug. 27, 1977 [DE] Fed. Rep. of Germany ....... 2738717
Dec. 24, 1977 [DE] Fed. Rep. of Germany ....... 2758025

[51] Int. Cl.³ .......................................... A61K 31/445
[52] U.S. Cl. ..................................... 424/267; 424/249; 424/250; 424/251; 424/252; 424/258; 536/18; 544/105; 544/216; 544/238; 544/277; 544/322; 544/336; 546/143; 546/159; 546/188; 546/197; 546/199; 546/200; 546/201; 546/207; 546/208; 546/210; 546/211; 546/212; 546/214; 546/215; 546/219; 546/220; 546/243
[58] Field of Search ................. 424/267; 546/242, 219, 546/220, 243, 215

[56] References Cited
U.S. PATENT DOCUMENTS
4,065,562 12/1977 Ohata et al. ........................... 424/267
4,182,767 1/1980 Murai et al. ...................... 546/242 X

*Primary Examiner*—Henry R. Jiles
*Assistant Examiner*—Richard A. Schwartz
*Attorney, Agent, or Firm*—Sprung, Felfe, Horn, Lynch & Kramer

[57] ABSTRACT

The invention includes certain 3,4,5-trihydroxypiperidine compounds, methods for their preparation, compositions containing said 3,4,5-trihydroxypiperidine compounds and methods for the use of said compounds and compositions.

The subject matter of the invention is useful against diabetes, hyperlipaemia and adiposity as well as in animal nutrition.

3 Claims, No Drawings

ANIMAL FEEDSTUFFS EMPLOYING 3,4,5-TRIHYDROXYPIPERIDINES

This is a division of application Ser. No. 936,280, filed Aug. 23, 1978, now pending.

The present invention relates to certain new 3,4,5-trihydroxypiperidine compounds, to several processes for their production and to their use as medicaments, in particular as agents against diabetes, hyperlipaemia and adiposity, and in animal nutrition, for influencing the lean meat/fat ratio in favour of the proportion of lean meat.

The present invention provides compounds which are 3,4,5-trihydroxypiperidines of the following general formula or their pharmaceutically acceptable salts and bioprecursors:

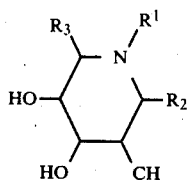

in which $R_1$ and $R_3$ are the same or different and each is H or an optionally substituted, straight-chain, branched or cyclic saturated or unsaturated aliphatic hydrocarbon radical e.g. alkyl, alkenyl or alkinyl or an optionally substituted carbocyclic aromatic or heterocyclic radical, and $R_2$ is —H, —OH, —OR', —SH, —SR', —NH$_2$, —NHR',

NH$_2$CH$_2$—, NHR'—CH$_2$—, NR'R''—CH$_2$—, —COOH, —COOR', HO—CH$_2$—, R'CO—NHCH$_2$—, R'CO—NR''CH$_2$—, R'SO$_2$NHCH$_2$—, R'SO$_2$—NR''CH$_2$—,

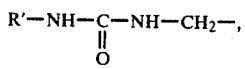

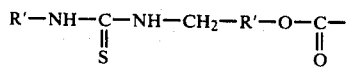

NH—CH$_2$—, —SO$_3$H, —CN, —CONH$_2$, —CONHR' or —CONR'R'', wherein R' and R'' are the same or different and each has any of the meanings given above for $R_1$, provided that when $R_3$ is —CH$_2$OH and $R_2$ is H or OH;

$R_3$ is H and $R_2$ is H, OH, SO$_3$H, —CN or CH$_2$—NH$_2$; or $R_3$ is —CH$_2$—NH$_2$ and $R_2$ is OH, then $R_1$ is not H.
$R_3$ preferably is —H, —CH$_3$, —CH$_2$OH, —CH$_2$—NH$_2$, NHR'— CH$_2$—, NR'R''—CH$_2$—, R'CONH—CH$_2$—, R'CO—NR''CH$_2$—, Hal-CH$_2$—, R'O—CH$_2$—, R'COOCH$_2$—, R'SO$_2$O—CH$_2$—, R'SO$_2$NHCH$_2$—, R'SO$_2$—NR''CH$_2$—, R'NH—CO—NH—CH$_2$—, R'NHCS—NH—CH$_2$—, R'O—CO—NH—CH$_2$—, —CN, —COOH, —COOR', —CONH$_2$, —CONHR' or —CONR'R'', wherein R' and R'' are the same or different and each has any of the meanings given above for $R_1$.

For the purpose of this specification the term pharmaceutically acceptable bioprecursor' of an active compound of the invention means a compound having a structural formula different from the active compound but which nonetheless, upon administration to a warm-blooded animal is converted in the patient's body to the active compound.

Suitable pharmaceutical acceptable salts are e.g. chlorides, sulfates, acetates, carbonates and oxalates.

$R_1$, R' and R'' are the same or different and preferably each is alkyl having from 1 to 30, desirably from 1 to 18, and more desirably from 1 to 10 C atoms, alkenyl or alkinyl having from 2 to 18, desirably from 3 to 10, C atoms, a monocyclic, bicyclic or tricyclic aliphatic radical having from 3 to 10 C atoms, which can be saturated, mono-unsaturated or di-unsaturated, carbocyclic particularly cycloalkyl, cycloalkenyl or cycloalkinyl having 3 to 8 carbon atoms, such as cyclopentyl, cyclohexyl, cyclopentenyl, cyclohexenyl, cyclopentadienyl or cyclohexadienyl aryl having 6 or 10 C atoms, such as phenyl or naphthyl, or a heterocyclic radical having from 3 to 8, in particular from 3 to 6, ring members which can contain 1, 2, 3 or 4 hetero-atoms, each of which is preferably N, O or S, and to which a benzene ring or a further said heterocyclic radical can be fused, each of the above groups being optionally substituted by from 1 to 5, most preferably by 1, 2 or 3, substituents.

Examples which may be mentioned of substituents for alkyl are: hydroxyl, and alkoxy having preferably from 1 to 4 carbon atoms, in particular methoxy and ethoxy; acyloxy, the acyl radical being derived from an aliphatic (particularly alkane) carboxylic acid having from 1 to 7 C atoms, an aromatic carboxylic acid, most preferably a phenyl-carboxylic acid, such as benzoic acid, phthalic acid, etc, optionally substituted in the phenyl moiety by one, two or more of —OH, -halogen, preferably F, Cl or Br, C$_1$ to C$_4$-alkyl, C$_1$ to C$_4$-alkoxy, nitro and/or amino, or a heterocyclic carboxylic acid which is derived from a 5-membered or 6-membered heterocyclic compound containing from 1 to 3 hetero-atoms each of which is N, O or S and optionally substituted in the heterocyclic ring moiety by C$_1$ to C$_4$-alkyl, chlorine, bromine or amino; amino, monoalkylamino and dialkylamino having preferably from 1 to 4 carbon atoms in each alkyl moiety, most preferably monomethylamino, monoethylamino, dimethylamino and diethylamino, and monoacylamino, the acyl moiety being derived from an aliphatic (particularly alkane) carboxylic acid having from 1 to 7 C atoms, an aromatic carboxylic acid, most preferably a phenyl-carboxylic acid, such as benzoic acid, phthalic acid, etc., optionally substituted in the phenyl moiety by -OH, -halogen, most preferably F, Cl or Br, C$_1$ to C$_4$-alkyl, C$_1$ to C$_4$-alkoxy, nitro and/or amino, or a heterocyclic carboxylic acid which is derived from a 5-membered or 6-membered heterocyclic compound containing from 1 to 3 hetero-atoms each of which is N, O or S and optionally substituted in the heterocyclic ring moiety by C$_1$ to C$_4$-alkyl, chlorine, bromine or amino; mercapto, or alkylthio having preferably from 1 to 4 carbon atoms, in particular methylthio or ethylthio; halogen, preferably fluorine, chlorine or bromine; alkylcarbonyl having preferably from 1 to 4 carbon atoms in the alkyl moiety; carboxyl, nitro, cyano, an aldehyde group or a sulphonic acid group; or a heterocyclic radical of the above mentioned type, or most preferably, a heterocyclic radical which is derived from a sugar, preferentially from a hexose or pentose, which can be bonded to the alkyl moiety directly via a ring atom or via an —O—, —S— or —NH— bridge.

Examples of heterocyclic substituents of the alkyl are: phthalimido, pyridyl, thienyl, furyl, isoxazolyl, thiazolyl, glucopyranosyl, ribofuranosyl, oxiranyl and the like. Further suitable substituents of the alkyl are aromatic radicals, such as naphthyl and in particular phenyl, optionally having one or more, preferably from 1 to 3, identical or different substituents each of which is -OH, —$NH_2$, $C_1$ to $C_4$-alkyl-NH—, $C_1$ to

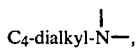

$C_4$-dialkyl-N—, $C_1$ to $C_4$-alkoxy, $NO_2$, —CN, —COOH, —COO-alkyl ($C_1$ to $C_4$), $C_1$ to $C_6$-alkyl, halogen, most preferably fluorine, chlorine or bromine, $C_1$ to $C_4$-alkylthio, —SH, $C_1$ to $C_4$-alkylsulphonyl, —$SO_3H$, —$SO_2$—$NH_2$ and —$SO_2$—NH-alkyl ($C_1$ to $C_4$). The alkyl can also have a monocyclic, bicyclic or tricyclic aliphatic substituent having preferably from 3 to 10 carbon atoms, which in turn can be substituted by hydroxyl, amino, halogen, most preferably fluorine, chlorine or bromine, or —COOH.

The alkyl preferably is substituted by hydroxyl, alkoxy having from 1 to 4 carbon atoms, mercapto, alkylthio, having from 1 to 4 carbon atoms, halogen, nitro, amino, mono alkylamine having from 1 to 4 C ato ms and acylamino, the acyl moiety being derived from an aliphatic carboxylic acid having from 1 to 6 C atoms.

Possible substituents for the monocyclic, bicyclic or tricyclic radicals $R_1$, R' and R" are the substituents quoted hereinabove for alkyl.

The aryl radicals can have one or more, preferably from 1 to 3, identical or different substituents. Examples of substituents which may be mentioned are: alkyl having from 1 to 10 C atoms, which can in turn themselves be substituted, for example by chlorine, nitro or cyano; optionally substituted alkenyl having from 1 to 10 carbon atoms; hydroxyl, alkoxy having preferably from 1 to 4 carbon atoms; amino, and monoalkylamino and di-alkylamino having preferably from 1 to 4 carbon atoms per alkyl moiety; mercapto, and alkylthio having preferably from 1 to 4 carbon atoms; carboxyl, carbalkoxy having preferably from 1 to 4 carbon atoms, the sulphonic acid group, alkylsulphonyl having preferably from 1 to 4 carbon atoms and arylsulphonyl, preferably phenylsulphonyl; aminosulphonylsulphonyl, and alkylaminosulphonyl and dialkylaminosulphonyl having from 1 to 4 carbon atoms per alkyl moiety, preferably methylaminosulphonyl and dimethylaminosulphonyl; nitro, cyano or the aldehyde group; alkylcarbonylamino having preferably from 1 to 4 carbon atoms; and alkylcarbonyl having from 1 to 4 carbon atoms, benzoyl, benzylcarbonyl and phenylethylcarbonyl, the last-mentioned alkyl, phenyl, benzyl and phenylethyl being in turn themselves optionally substituted, for example by chlorine, nitro or hydroxyl.

The heterocyclic radicals $R_1$ are preferably derived from hetero-paraffinic, hetero-aromatic or hetero-olefinic 5-membered or 6-membered rings having preferably from 1 to 3 identical or different hetero-atoms, each of which is oxygen, sulphur or nitrogen. These ring systems can carry further substituents, such as, for example, hydroxyl, amino or $C_1$ to $C_4$-alkyl, or benzene or other, preferably 6-membered, heterocyclic rings of the type mentioned hereinabove can be fused to them.

Particularly preferred heterocyclic radicals are derived, for example, from furane, pyrane, pyrrolidine, piperidine, pyrazole, imidazole, pyrimidine, pyridazine, pyrazine, triazine, pyrrole, pyridine, benzimidazole, quinoline, isoquinoline or purine.

In the compounds of the formula I, $R_2$ preferably represents —H, —OH, —$SO_3H$, —CN, —$CH_2NH_2$, —$CH_2NH$—($C_1$ to $C_{14}$-alkyl),

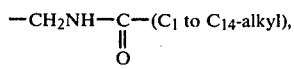

—$CH_2$—NH—$SO_2$($C_1$ to $C_{14}$)-alkyl or —$CH_2$—N-H—$SO_2$-phenyl. $R_2$ very particularly preferably represents —H, —$SO_3H$ or —CN.

$R_3$ preferably represents hydrogen, —$CH_2$—OH, —$CH_3$, —$CH_2NH_2$, —$CH_2NH$—($C_1$ to $C_6$-alkyl),

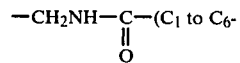

alkyl) or —$CH_2$—O—($C_1$-$C_6$-alkyl).

However, $R_3$ very particularly preferably represents —$CH_2OH$.

It has been found that the new compounds of the formula I are potent inhibitors for α-glucosidases, in particular for disaccharidases. The new compounds are thus valuable agents for influencing a number of metabolic processes and thus constitute an enrichment of pharmacy.

Furthermore the compounds of the formula I, especially those with $R_1$=$C_6$ to $C_{10}$-n-alkyl are inhibitors for the triglycerid and cholesterol absorption. Compared with 2-hydroxymethyl-3,4,5-trihydroxypiperidine, which is known from DT-OS (German Published Specification) No. 2,656,602, the new compounds have advantageous therapeutic properties.

The present invention further provides a process for the production of a compound according to the invention in which a compound of the general formula II or IIa

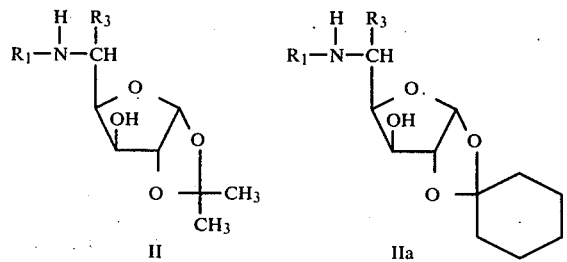

in which $R_1$ and $R_3$ have the same meaning as defined hereinbefore in formula I, is subjected to acid hydrolysis so as to remove the isopropylidene or cyclohexylidene protective group, it sometimes being advantageous to isolate the compound of the formula I in the form of an adduct of sulphurous acid or of hydrocyanic acid ($R_2$=$SO_3H$ or CN). The compounds of the formula I in which $R_2$ is OH can be liberated from the bisulphite addition products by treatment with bases, preferably alkaline earth metal hydroxides, such as Ca(OH)$_2$ or Sr(OH)₂, but most preferably Ba(OH)₂. The compounds of the formula I in which R₂ is H can be obtained from compounds of the formula I in which R₂ is OH by reaction with hydrogen donor reducing agents, such as, for example, NaBH₄.

Furthermore, it has been found that a compound of the formula I can be obtained when a compound of the formula I in which R₂ is OH is reacted with hydrocyanic acid in a manner which is in itself known so as to produce a compound of the formula I in which R₂ is CN, and a compound in which R₂ is —CH₂NH₂ is optionally obtained from the products by catalytic hydrogenation of the nitrile group, and the amino group is optionally acylated, alkylated or sulphonylated in a manner which is in itself known so as to produce a compound of the formula I in which R₂ is R′CONCH₂—, R′CONR″CH₂—, NHR′—CH₂—, NR′R″—CH₂— or R′SO₂NHCH₂—, wherein R′ and R″ having the same meaning as defined hereinbefore in formula I.

A compound of the formula I in which R₂ is —OR′, —SH, —SR′, —NH₂, —NHR′ or —NR′R″ can be obtained by reacting a compound of the formula I in which R₂ is —OH with an alcohol R′OH), H₂S, mercaptan (R′SH), ammonia or amine (H₂NR′ or HNR′R″), wherein R′ and R″ have the same meaning as defined hereinbefore in formula I in a manner which is in itself known.

A compound of the formula I in which R₂ is —COOH may be obtained by hydrolysis of a compound of the formula I in which R₂ is —CN in a manner which is in itself known.

In a manner which is in itself known, a compound of the formula I in which R₂ is —COOR′ may be obtained from the resulting carboxylic acid by reaction with an alcohol (R′OH), and a compound of the formula I in which R₂ is —CONHR′ or —CONR′R″ or —CONH₂ may be obtained by aminolysis of a resulting ester with NH₃, R′NH₂ or R′R″NH, wherein R′ and R″ have the same meaning as defined hereinbefore in formula I.

A compound of the formula I in which R₂ is -OH may also be obtained when a compound of the formula II is reacted with trifluoroacetic anhydride (reaction step A) so as to produce a compound of the formula III, the isopropylidene protective group being then split off by acid hydrolysis (reaction step B) and the trifluoroacetyl group in the compound IV is subsequently removed in the neutral to alkaline reaction medium (reaction step C).

The reaction sequence indicated may be illustrated as follows:

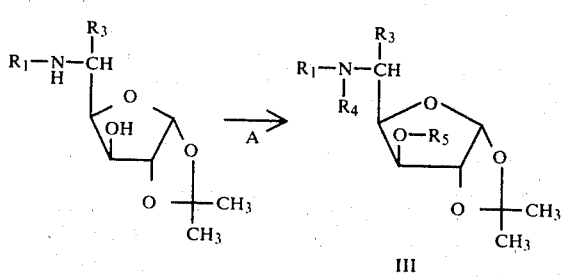

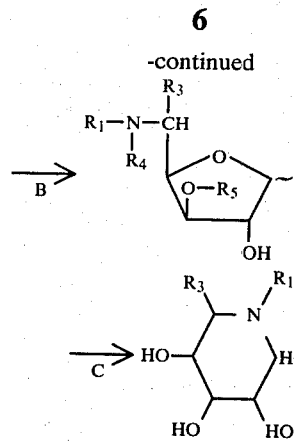

In the above formulae, R₁ and R₃ have the same meaning as defined hereinbefore in formula I, and R₄ is trifluoroacetyl and R₅ is trifluoroacetyl or hydrogen.

An analogous reaction sequence is applicable to the compounds of the formula IIa.

It has also been found that a compound of the formula I in which R₂ is H can be obtained when a compound of the general formula V

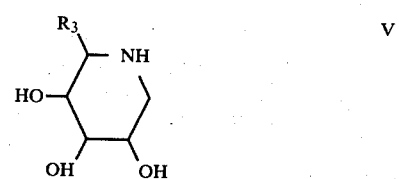

wherein R₃ has the same meaning as defined hereinbefore in formula I, is reacted with a carbonyl compound of the general formula VI

in which

R₆ and R₇ are the same or different and each has the same meaning as given for R₁ or R₆ and R₇ are members of an alicyclic or heterocyclic ring, in the presence of a hydrogen donor reducing agent.

A compound of the formula I in which R₂ is H may also be obtained by reaction of:

an amide of the following general formula VII or a derivative thereof with hydroxyl-protective groups

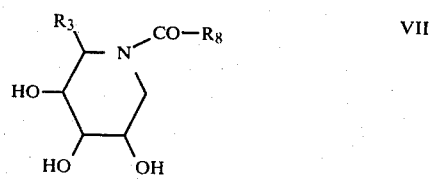

in which R₃ has the same meaning as defined hereinbefore in formula I and R₈ has the same possible meanings as given for R₁ in formula I, or a carbamate of the following general formula VIII or a derivative thereof provided with hydroxyl-protective groups

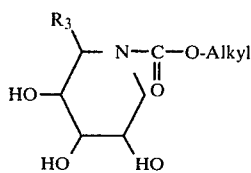

is reduced to the corresponding amine with an amide-reducing agent.

A further process for the preparation of compounds of the formula I in which $R_2$ is H comprises reaction of a compound of the formula V with a reactive alkylating agent of the formula IX $$Z-R_1 \qquad \text{IX}$$

wherein $R_1$ is alkyl having the same meaning as in formula I hereinabove and

Z is an easily eliminated leaving group, such as, for example, halide or $^\ominus O\text{—}SO_3H$, which is customary in alkylating agents.

In addition, in a compound of the formula I in which $R_3$ is —$CH_2OH$, the —$CH_2OH$ group can be selectively converted into a

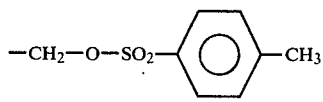

group in a manner which is in itself known and this then either converted into a —$CH_3$ group by reduction or into an amino group by reduction, via a —$CH_2$—$N_3$ group. Compounds of the formula I may also be obtained when, in a compound of the formula I in which $R_3$ is —$CH_2$—$NH_2$, derivatives of the amino group, are prepared by reaction with aldehydes or ketones in the presence of a hydrogen donor or with carboxylic acid chlorides or sulphonic acid chlorides, chlorocarbonic acid esters, isocyanates, isothiocyanates, and alkyl halides, in a manner which is in itself known.

Compounds of the formula I in which $R_1$ is an aliphatic or aromatic radical which is substituted by an acylamino, sulphonylamino, alkoxycarbonylamino, ureido or thioureido group can be obtained starting from compounds of the formula I in which $R_1$ is an aliphatic or aromatic radical which is substituted by an amino group, by reacting this amino group with a carboxylic acid chloride or sulphonic acid chloride or with a chlorocarbonic acid ester, isocyanate or isothiocyanate in a manner which is in itself known.

The individual procedures for the preparation of the active compounds according to the invention are illustrated, by way of example only, below:

If a compound of the formula II in which $R_1$ is ethyl is used as a starting material, the course of a suitable reaction can be represented as follows:

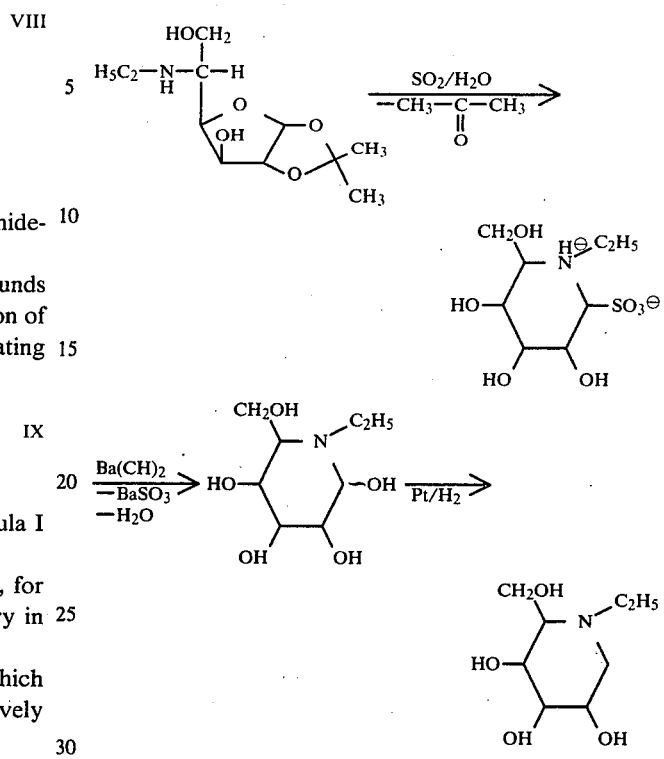

If 1-desoxynojirimycin (a compound of the general formula V) and formaldehyde are used as starting materials, a suitable reaction can be represented as follows:

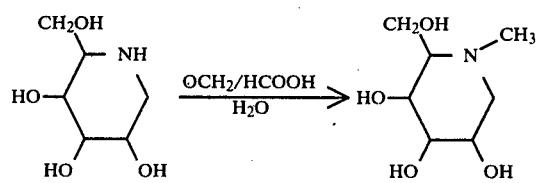

If benzaldehyde is used as the carbonyl component, reductive alkylation may be carried out as follows:

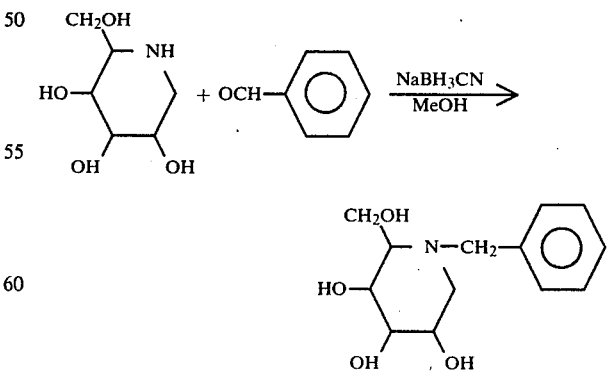

If an acid amide of the general formula VII is used as starting material, a suitable reaction can be described as follows:

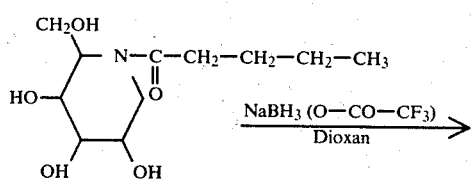

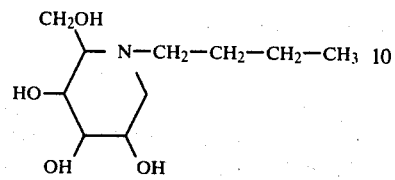

Urethanes of the general formula VIII, optionally in the form of derivatives provided with hydroxyl-protective groups, may be reduced to N-methyl-1-desoxynorjirimycin with LiAlH$_4$:

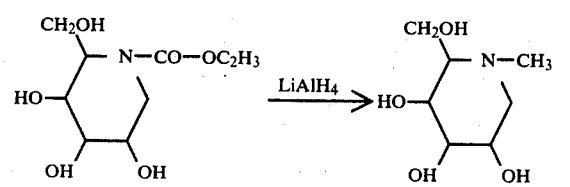

For the reaction of 1-desoxynorjirimycin with an alkylating agent, the reaction with allyl bromide can be indicated by way of example as follows:

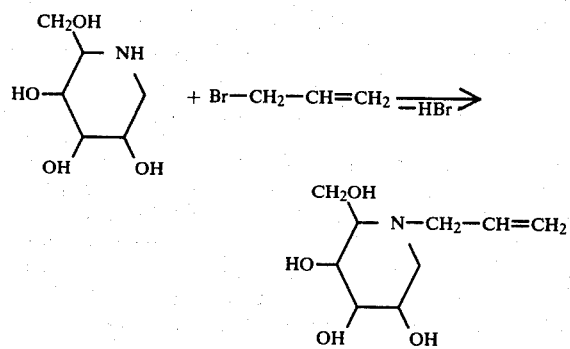

Some of the compounds of the formula II used as starting materials are known. This is the case where R$_3$ is H, —CH$_2$OH or —CH$_2$NH$_2$ and R$_1$ is H. Other compounds of the formula II or IIa are new; however, they can be prepared from compounds which are known from the literature by processes which are in themselves known.

Thus, for example, it is possible to use the compound of the formula X, which is known from the literature,

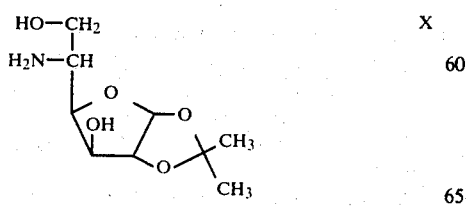

as a starting material and to react this with a carbonyl compound of the formula VI in the presence of a hydrogen donor reducing agent so as to produce a compound of the formula II.

Furthermore, it is possible to react the compound X with reactive acid derivative so as to produce an acid amide or urethane and to reduce this to an amine with an amide-reducing agent.

This can be illustrated by the following example:

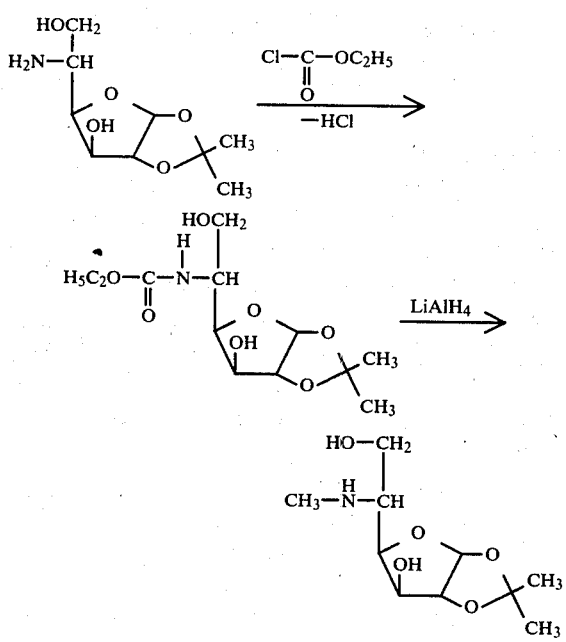

The compound of the formula X can also be reacted with reactive alkylating agents of the following general formula IX as defined hereinbefore $$Z—R_1 \qquad \text{IX}$$

so as to produce a compound of formula II.

Furthermore, in the above mentioned reactions, instead of the compound X it is also possible to employ known partially protected derivatives of the formula XI

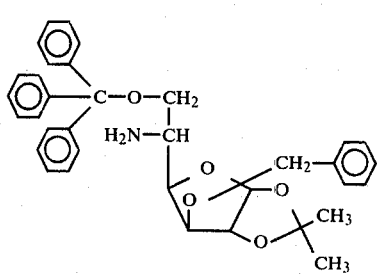

and then to remove the trityl and benzyl protective groups in a known manner, for example with sodium in liquid ammonia. To prepare compounds of the formula II, it is also possible to react the compound of formula XII, which is likewise known from the literature,

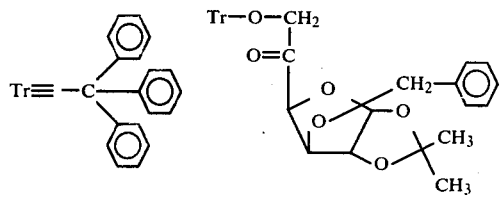

with an amine of the general formula XIII

 XIII wherein $R_1$ has the same meaning as defined hereinbefore in formula II, in the presence of a hydrogen donor reducing agent, for example in the presence of $NaBH_3OH$. As a rule, a diastereomer mixture is formed in this reaction. The diastereomer which is not desired may be appropriately separated off at this stage or at a later stage by the customary chromatographic methods or by fractional crystallisation. Finally, the trityl and benzyl protective groups can be split off in a known way, for example with sodium in liquid ammonia.

Moreover, new compounds of the formula II or IIa can also be obtained by reaction of one or more of the degradation products of D-glucose, which are known from the literature, of the formulae XIV or XVI

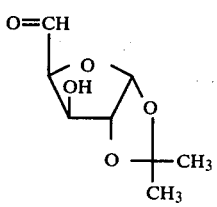

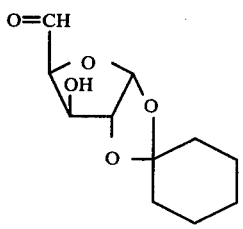

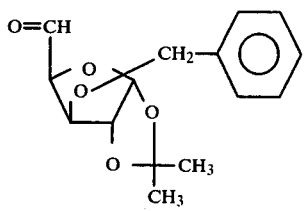

with an appropriate reagent having a carbanion character, such as, for example, alkyl-Li or Grignard compounds or the Li salt of 1,3-dithiane, so as to introduce a group $R_3$ as defined hereinbefore in formula I, and converting the resulting compound(s) of formula XVII

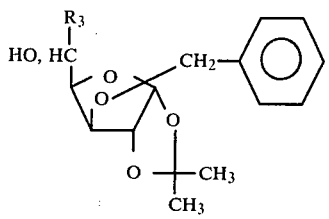

in which $R_3$ has the same meaning as defined hereinbefore in formula I, into the corresponding amine(s) in a manner which is in itself known [S. INOUYE et al., Tetrahedron 23, 2125-2144] via the ketone and the oxime, whereupon, as a rule, a mixture of the gluco compound and ido compound forms, from which the desired gluco compound of formula XVIII

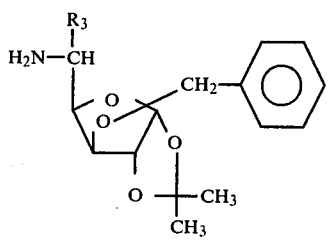

in which $R_3$ has the same meaning as defined immediately hereinbefore, can be isolated by customary chromatographic methods.

Removal of the benzyl protective group conveniently by catalytic hydrogenation or with Na in liquid $NH_3$, then gives the corresponding compound(s) of the formula II.

Compounds of the formula XIX (below) can be obtained when an appropriate aldehyde of any of the formulae XIV to XVI is reacted with an appropriate amine and hydrocyanic acid in a manner which is in itself known so as to produce an aminonitrile thereby introducing a group $R_1$ as defined hereinbefore in formula I. Thus for example a compound of formula XVI is reacted to produce a compound of formula XIX

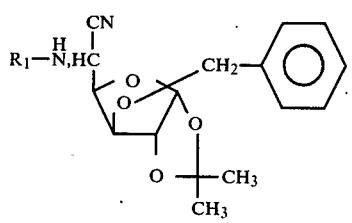

wherein $R_1$ has the same meaning as defined hereinbefore in formula I, and in this case also, as a rule, the desired gluco compound must be separated off from the ido compound by customary chromatographic methods. Further conversion of the nitrile group by hydrogenation or hydrolysis before or after the removal of the benzyl protective group leads to further compounds of the formula II.

The reaction of a compound of formula XIV, XV or XVI with a CH-acid compound, such as, for example, a nitroalkane, alkylnitrile, CH-acid ester or ketone can also lead to compounds of the formula II. In this case, unsaturated compounds, for example compounds of the formula XX, can be obtained:

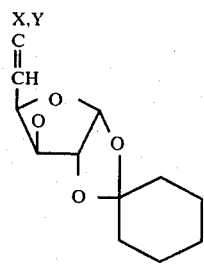

wherein X is —NO$_2$, —CN or —COOalkyl, and

Y is H, alkyl or aryl, either directly or by dehydration of the aldol addition product, and these compounds yield compounds of the formula IIa by a Michael addition reaction with an amine, after chromatographic separation of gluco and ido isomers.

The isopropylidene protective group can be split off from a compound of the formula II in a moderately strongly acid to weakly acid solution, preferably at a pH in the range from 1 to 4, in aqueous solution or in a water-miscible, water-containing organic solvent. Acids which can be used are dilute mineral acids, such as, for example, sulphuric acid, or also organic acids, such as acetic acid. The reaction is preferably carried out under atmospheric pressure and at a temperature from room temperature to the boiling point of the solvent.

In order to work up the reaction mixture, the acid is desirably neutralized and separated off as a salt or with the aid of a basic ion exchanger. The isolation of the compounds of formula I in which R$_2$ is OH may then appropriately be effected by careful removal of the solvent, for example by lyophilisation.

A preferred embodiment of the process of splitting off of the isopropylidene protective group from a compound of the formula II comprises saturation of the aqueous or water-containing alcoholic solution of the compound of the formula II with SO$_2$ and storing the saturated solution at a temperature of from 20° to 50° C. for several days. The compounds of the formula I can then be obtained as bisulphite adducts (R$_2$=—SO$_3$H), which in most cases readily crystallize, from which the compounds of the formula I can be liberated with the aid of, for example, aqueous Ba(OH)$_2$.

A compound of the formula I in which R$_2$ is OH can be reduced to a compound of the formula I in which R$_2$ is H by using an alkali metal borohydride, alkali metal cyanoborohydride or dialkylaminoborane. It is preferable to use sodium borohydride in aqueous solution or in a water-miscible water-containing organic solvent, such as, for example, dioxane, at room temperature or optionally elevated temperature. However, the reduction is very particularly preferably carried out catalytically with Pt or Pd as the catalyst or in the presence of Raney Ni. In this procedure, it is preferably carried out in an aqueous solution at room temperature.

Compounds of the formula I are further obtained from compounds of the formula

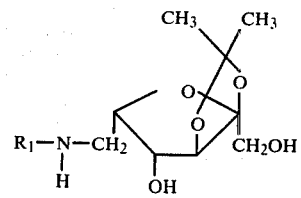

by hydrolysis with strong mineral acid of pH<1 at −20° to +20° C. and subsequent hydrogenation at pH 4 to 6 with for instance H$_2$/Raney-Nickel, H$_2$/P+O$_2$ or sodium borohydride.

The compound of the formula XXi can be prepared from compounds of the formula

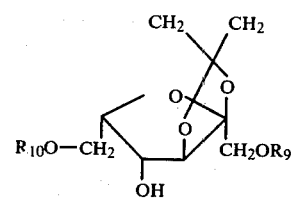

wherein R$_9$ is hydrogen or acetyl and R$_{10}$ is mesyl or tesyl, by reaction with amines of the formula

R$_1$—NH$_2$ at 20° to 150° C. in a polar solvent, e.g. an alkohol, dimethylsulfoxide or in an excess of the amine.

The starting material of the general formula V, in which R$_3$ is —CH$_2$OH, is known and can be obtained either by catalytic hydrogenation of nojirimycin, which is obtainable by fermentation [G. INOUYE et al., Tetrahedron 23, 2125–2144 (1968)], or by extraction from mulberry tree bark (see DT-OS (German Published Specification) No. 2,656,602), or entirely synthetically. 1-Desoxynojirimycin can also be conveniently prepared by a new advantageous process comprising cultivating an organism of the Bacillaceae family in a customary fermentation vessel in a customary nutrient medium at a temperature of from about 15° to about 80° C. for from about 1 to about 8 days, with aeration, centrifuging off the cells and isolating the desoxy compound from the culture broth or the cell extracts by a customary purification process (see German Patent Application No. P 26 58 563.7).

The carbonyl compounds of the formula VI are either known or can be prepared by standard processes. Typical examples which may be mentioned and preferably contain up to 8 carbon atoms, are: straight-chain or branched alkylaldehydes, such as formaldehyde, acetaldehyde, n-propanal, n-butanal, 2-methylpropanal, n-pentanal, 2-methylbutanal, 3-methylbutanal, 2,2-dimethyl-propanal, n-hexanal, 2-ethylbutanal, n-heptanal and n-octanal; alkenylaldehydes, such as propanal, 2-methylpropanal, 2-butenal, 2-methyl-2-butenal and 2-ethyl-2-hexenal; cyclic (particularly cycloalkyl aldehydes) aldehydes, such as cyclopropanecarbaldehyde, cyclopentanecarbaldehyde, cyclopentaneacetaldehyde and cyclohexanecarbaldehyde; benzaldehyde, o-, m- or p-toluenecarbaldehyde and phenylacetaldehyde; straight-chain and branched alkylaldehydes which are substituted by hydroxyl, such as 5-hydroxypentanal, 2-hydroxy-3-methylbutanal, 2-hydroxy-2-methylpropanal, 4-hydroxybutanal, 2-hydroxypropanal and 8-hydroxyoctanal; straightchain and branched alkylaldehydes which are substituted by amino, such as 5-aminopentanal, 2-aminopropanal, 3-aminopropanal, 4-aminobutanal, 2-amino-3-methylbutanal, 8-amino-octanal and mono-N-alkyl derivatives thereof; and straight-chain and branched alkylaldehydes which are disubstituted by amino and hydroxyl, such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal and mono-N-alkyl derivatives, particularly $C_1$-$C_8$-N-alkyl, thereof.

Furthermore: methoxy-acetaldehyde, ethoxy-acetaldehyde, n-propoxy-acetaldehyde, i-propoxy-acetaldehyde, n-butoxy-acetaldehyde, i-butoxy-acetaldehyde, tert.-butoxyacetaldehyde, cyclopropyl-methoxy-acetaldehyde, cyclopropoxyacetaldehyde, 2-methoxy-ethoxy-acetaldehyde, 2-ethoxy-ethoxyacetaldehyde, 2-methoxy(1-methyl-ethoxy)-acetaldehyde, 2-ethoxy(1-methyl-ethoxy)-acetaldehyde, phenoxy-acetaldehyde, 2-methoxy-2-methyl-acetaldehyde, 2-ethoxy-2-methyl-acetaldehyde, 2-n-propoxy-2-methyl-acetaldehyde, 2-(i-propoxy)-2-methyl-acetaldehyde, 2-(n-butoxy)-2-methyl-acetaldehyde, 2-(i-butoxy)-2-methyl-acetaldehyde, 2-(tert.-butoxy)-2-methyl-acetaldehyde, 2-cyclopropylmethoxy-2-methyl-acetaldehyde, 2-cyclopropoxy-2-methyl-acetaldehyde, 2-methoxy-ethoxy-α-methyl-acetaldehyde, 2-ethoxy-ethoxy-α-methyl-acetaldehyde, 2-methoxy-(1-methyl-ethoxy)-α-methyl-acetaldehyde, 2-methoxy-2,2-dimethylacetaldehyde, 2-ethoxy-2,2-dimethylacetaldehyde, 2-cyclopropylmethoxy-acetaldehyde, 2-ω-butoxy-2,2-dimethyl-acetaldehyde, methylthio-acetaldehyde, ethylthio-acetaldehyde, n-propylthio-acetaldehyde, i-propylthioacetaldehyde, cyclopropyl-methylthioacetaldehyde, 3-methoxy-propanal, 3-ethoxy-propanal, 3-n- and 3-i-propoxypropanal, 3-n-, 3-i- and 3-tert.-butoxy-propanal, 3-cyclopropoxy-propanal, 3-cyclopropylmethoxy-propanal, 3-methoxy-3-methyl-propanal, 3-ethoxy-3-methyl-propanal, 3-n- and 3-i-propoxy-3-methyl-propanal, 3-n-, 3-i- and 3-tert.-butoxy-3-methyl-propanal, 2,3- and 4-methoxy-butanal, 2-,3- and 4-ethoxy-butanal, 2-methylthio-propanal, 2-ethylthio-propanal, 3-methyl-thio-propanal, 3-ethylthio-propanal, 2-methylthio-butanal, 3-methylthio-butanal, 4-methyl-thiobutanal, furfurol, tetrahydrofurfurol, thiophene, 5-bromothiophene, 5-methylfurfurol and pyrane-carbaldehyde.

In addition, examples of ketones which may be mentioned are particularly those which are hydrocarbon except for the oxo groups but also those containing additional substituents, such as $C_1$-$C_4$-alkoxy and nitro: acetone, methyl ethyl ketone, methyl n-propyl ketone, diethyl ketone, methyl butyl ketone, cyclopentanone, di-n-propyl ketone, cyclohexanone, 3-methylcyclohexanone, 4-methylcyclohexanone, acetophenone, propiophenone, butyrophenone, phenylacetone, p-methoxyacetophenone and m-nitroacetophenone.

Formic acid, for example, can be used as the hydrogen donor reducing agent (Leuckart-Vallach reaction). The formic acid is generally used in a large excess. If formaldehyde is used as the carbonyl reaction component, the reaction can be carried out in aqueous solution, and if ketones and less reactive aldehydes are used, it can be carried out in anhydrous formic acid. The reaction temperature is generally from 100° to 200° C., and if appropriate the reaction should be carried out in an autoclave.

Catalytically activated hydrogen can also be used as the hydrogen donor reducing agent. A possible catalyst is most preferably, Raney nickel, but noble metal catalysts, particularly those of Group VIII of the Periodic System, can also be used. In general, the reaction is carried out under a pressure of from 80 to 150 atmospheres of $H_2$ pressure and at a temperature of from 70° to 150° C. Preferred solvents are protic, polar solvents, especially alcohols, more particularly alkanols, such as methanol, ethanol, propanol and isopropanol.

Alkali mmetal cyanoborohydrides, dialkylaminoboranes and alkali metal borohydrides can also be used as hydrogen donor reducing agents. In this process variant, the use of sodium cyanoborohydride is particularly preferred.

In general, the reaction is carried out at room temperature. However, it can also be advantageous to heat the mixture to the reflux temperature of the reaction medium.

The process is usually carried out in an inert solvent. Although anhydrous aprotic solvents can be employed (for example tetrahydrofurans, when the reducing agent is morpholinoborane), a protic solvent is usually used. A suitable protic solvent is, in particular, a lower alkanol. However, water or an aqueous lower alkanol (for example aqueous methanol or ethanol) or other aqueous solvent system, such as, for example, aqueous dimethylformamide, aqueous hexamethylphosphoric acid triamide, aqueous tetrahydrofurane or aqueous ethylene glycol dimethyl ether, may also be used.

The process is usually carried out in a pH range of from 1 to 11, though a pH range of from 4 to 7 is preferred.

The acid amides of the general formula VII and urethanes of the general formula VIII are known in some cases, or they can be obtained by known processes from a compound of formula V and a reactive acid derivative, which can also be formed in situ from the corresponding free acid.

In this procedure, the reaction can be carried out in a manner such that only the amino group of the compound of formula V reacts with the acid derivative, for example by using excess acid anhydride in an aqueous or alcoholic (e.g. $C_1$-$C_3$-alkanolic) solution, or such that the peracylated compounds first form and are then converted into the N-acylated compounds by reaction with alcoholic ammonia or by trans-esterification catalyzed by alkali metal alcoholate. The latter process can be illustrated by way of example by the following reaction scheme:

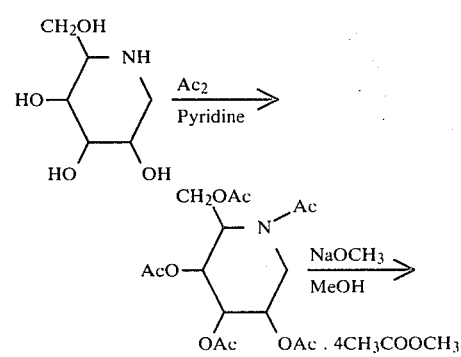

-continued $$\text{structure: piperidine ring with CH}_2\text{OH, N-Ac, HO, OH, OH substituents}$$

$$Ac = -\overset{\overset{\displaystyle O}{\|}}{C}-CH_3$$

An acid amide of the general formula II can be reduced to the corresponding amine of the formula I (R=H) with a complex metal hydride or with a boron hydride compound. It is preferable to use NaBH$_4$ in pyridine or a sodium acyloxyborohydride, particularly sodium trifluoroacetoxyborohydride. In general, the reducing agent is employed in excess. Sodium trifluoroacetoxyborohydride can be produced in situ from sodium borohydride and trifluoroacetic acid. Possible solvents are, in addition to pyridine, polar aprotic solvents, such as dioxane, tetrahydrofurane or diglyme. The reaction is preferably carried out at the boiling point of the solvent used. LiAlH$_4$ can also optionally be used for the reduction, preferably when the hydroxyl groups are first protected in the customary way.

The reactive alkylating agents of the general formula IX are known or can be prepared by customary processes. The reaction with a compound of formula V can be carried out in an inert organic solvent, generally at from room temperature up to the boiling point of the reaction medium, with or without the addition of an acid-binding agent.

Specific new active compounds according to the invention which may be mentioned are compounds of the formula:

$$\text{piperidine structure with CH}_2\text{CH, HO, HO, OH, N-R}_1$$

R$_1$
CH$_3$
CH$_3$CH$_2$—
CH$_3$CH$_2$CH$_2$—
CH$_3$CHCH$_3$
|
CH$_3$CH$_2$CH$_2$CH$_2$—
CH$_3$—CH—CH$_2$—CH$_3$
|

H$_3$C
   \
    CH—CH$_2$—
   /
H$_3$C

H$_3$C
   \
H$_3$C—C—
   /
H$_3$C

CH$_3$(CH$_2$)$_3$—CH$_2$—
H$_3$C
   \
    CH—CH$_2$—CH$_2$—
   /
H$_3$C

|
CH$_3$—CHCH$_2$CH$_2$CH$_3$

CH$_3$CH$_2$—CHCH$_2$CH$_3$
          |

CH$_3$CHCH$_2$CH$_2$—
   |
   CH$_3$

CH$_3$(CH$_2$)$_4$—CH$_2$—
CH$_3$(CH$_2$)$_5$—CH$_2$—

-continued $$\text{piperidine structure with CH}_2\text{CH, HO, HO, OH, N-R}_1$$

R$_1$

CH$_3$CHCH$_2$CH$_2$CH$_2$—
|
CH$_3$

CH$_3$CH—(CH$_2$)$_3$—CH$_2$—
|
CH$_3$

CH$_3$(CH$_2$)$_6$—CH$_2$—

CH$_3$CH—(CH$_2$)$_4$—CH$_2$—
|
CH$_3$

CH$_3$—(CH$_2$)$_8$—CH$_2$—
CH$_3$—(CH$_2$)$_{10}$—CH$_2$—
CH$_3$—(CH$_2$)$_{12}$—CH$_2$—
CH$_3$—(CH$_2$)$_{14}$—CH$_2$—
CH$_3$—(CH$_2$)$_{16}$—CH$_2$—

▷—CH$_2$—

⬠—CH$_2$—

⬡—CH$_2$—

⬠—CH$_2$—CH$_2$—

HO—CH$_2$—CH$_2$—
H$_3$C—CH—CH$_2$—
        |
        OH

HOH$_2$C—CH$_2$—CH$_2$—
HOH$_2$C—CH$_2$—CH$_2$—CH$_2$—
HOH$_2$C—(CH$_2$)$_3$—CH$_2$—
CH$_3$—CH—CH—CH$_2$—
      |    |
      CH$_3$ OH

HO—CH$_2$—CH—CH$_2$—
            |
            OH

CH$_3$OCH$_2$—CH$_2$—
C$_3$H$_7$OCH$_2$—CH$_2$—
CH$_3$COOCH$_2$—CH$_2$—

⌬—C—OCH$_2$CH$_2$CH$_2$CH$_2$—
   ‖
   O

H$_2$N—CH$_2$—CH$_2$—
H$_3$C
   \
    N—CH$_2$—CH$_2$—
   /
H$_3$C

CH$_3$CONH—CH$_2$—CH$_2$—

⌬—C—NH—CH$_2$—CH$_2$—
   ‖
   O

C$_2$H$_3$OCNH—CH$_2$—CH$_2$—
     ‖
     O

CH$_3$
         |
CH$_3$CO—N—CH$_2$—CH$_2$—
CH$_3$NH—CO—NH—CH$_2$CH$_2$—

⌬—NH—CO—NH—CH$_2$CH$_2$—

CH$_3$NH—CS—NH—CH$_2$CH$_2$—

⌬—NH—CS—NH—CH$_2$—CH$_2$—

H$_2$N—CH$_2$CH$_2$CH$_2$—
CH$_3$CONHCH$_2$CH$_2$CH$_2$—

⌬—CONHCH$_2$CH$_2$CH$_2$—

-continued

[Structure: cyclohexane ring with CH₂CH substituent, HO, HO, OH groups, and N-R₁]

| R₁ |
|---|
| CH₃NHCONHCH₂CH₂CH₂— |
| H₂N—CH₂CH₂CH₂CH₂— |
| H₂C=CH—CH₂— |
| H₃C—HC=CH—CH₂— |
| H₂C=CH—CH₂—CH₂— |
| H₂C=CH—CH₂—CH₂—CH₂—CH₂— |
| H₂C=CH—(CH₂)₇—CH₂— |
| HOOC—CH₂— |
| HOOC—CH₂—CH₂— |
| H₅C₂OOC—CH₂—CH₂— |
| H₂N—C(=O)—CH₂— |
| C₂H₅NH—C(=O)—CH₂— |
| C₄H₉—HN—C(=O)—CH₂— |
| HO₃S—CH₂CH₂CH₂— |
| H₂NO₂S—CH₂CH₂CH₂— |
| Ph-CH₂-C=CH—CH₂—CH₂—CH—COOH |
| 2-NO₂-C₆H₄-CH₂— |
| 3-Br-4-OH-C₆H₃-CH₂— |
| C₆H₅-C(=O)-CH₂— |
| 2-OH-3-OCH₃-C₆H₃— |
| H—C≡C—CH₂— |
| 4-HO-C₆H₄-CH₂— |
| 3-OCH₃-4-OH-5-NO₂-C₆H₂-CH₂— |
| 4-HO₃S-2-NO₂-C₆H₃-CH₂— |
| 3-O₂N-2-SO₃H-C₆H₃-CH₂— |
| 2-OH-3-OCH₃-5-OCH₃-C₆H₂-CH₂— |
| 2-SCH₃-C₆H₄-CH₂— |

-continued

[Structure: cyclohexane ring with CH₂CH substituent, HO, HO, OH groups, and N-R₁]

| R₁ |
|---|
| 4-NaO₃S-2-SO₃Na-C₆H₃-CH₂— |
| 2-Cl-4-NO₂-C₆H₃-CH₂— |
| 2-Cl-5-NO₂-C₆H₃-CH₂— |
| 2-Cl-3-NO₂-C₆H₃-CH₂— |
| 2-NO₂-4-Cl-C₆H₃-CH₂— |
| 2-Br-C₆H₄-CH₂— |
| 3-Br-C₆H₄-CH₂— |
| 4-Br-C₆H₄-CH₂— |
| 2-Cl-C₆H₄-CH₂— |
| 3-Cl-C₆H₄-CH₂— |
| 4-Cl-C₆H₄-CH₂— |
| 2-F-C₆H₄-CH₂— |
| 3-F-C₆H₄-CH₂— |
| 4-F-C₆H₄-CH₂— |
| 4-O₂N-C₆H₄-CH₂— |
| 2-NO₂-4-OH-C₆H₃-CH₂— |
| 2-NO₂-4-OH-C₆H₃-CH₂— |

-continued

[Structure: cyclohexane ring with CH₂CH substituent, HO, HO, OH, and N-R₁ groups]

R₁:
- 3-hydroxybenzyl (OH-C₆H₄-CH₂-)
- 4-hydroxybenzyl (HO-C₆H₄-CH₂-)
- 2-hydroxybenzyl
- 2,5-dihydroxybenzyl
- 3,4-dihydroxybenzyl (HO, HO substituted)
- 4-carboxybenzyl (HOOC-C₆H₄-CH₂-)
- 3,4-ethylenedioxybenzyl
- 2-hydroxy-5-carboxybenzyl (HO, COOH)
- 2-methylbenzyl (CH₃-C₆H₄-CH₂-)
- 4-methylbenzyl (H₃C-C₆H₄-CH₂-)
- 2-methoxybenzyl (OCH₃)
- 3-methoxybenzyl (OCH₃)
- 2-methoxy-4-hydroxybenzyl (OCH₃, HO)
- 3,4-dimethoxybenzyl (H₃CO, OCH₃)
- 3-methoxy-4-hydroxybenzyl (H₃CO, OH)
- 4-acetamidobenzyl (CH₃CONH-C₆H₄-CH₂-)
- 2,5-dimethylbenzyl (CH₃, CH₃)
- 2-ethoxybenzyl (OC₂H₅)

-continued

[Same cyclohexane ring structure with CH₂CH, HO, HO, OH, and N-R₁]

R₁:
- 4-methoxy-3-methylbenzyl (H₃CO, CH₃)
- 2,5-dimethoxybenzyl (OCH₃, OCH₃)
- 4-(N,N-dimethylamino)benzyl (H₃C\N/CH₃ on C₆H₄-CH₂-)
- 3,4,5-trimethoxybenzyl (H₃CO, OCH₃, OCH₃)
- 3,4,5-trimethoxybenzyl (H₃CO, OCH₃, OCH₃)
- CH₂—CH—CH₂—CH₂— (with epoxide O)
- phthalimido-propyl: isoquinoline-1,3-dione-N-CH₂-CH₂-CH₂-
- 2-pyridylmethyl
- 1-thio-β-glucosyl-ethyl (glucose-S-CH₂-CH₂-)
- β-glucosyl-oxyethyl (glucose-O-CH₂-CH₂-)
- 2-furylmethyl
- 2-thienylmethyl
- 3-indolylmethyl (indole-CH₂-)
- 5-bromo-2-thienylmethyl (Br-thiophene-CH₂-)
- 2-pyrrolylmethyl (pyrrole-N—CH₂-)
- 3-pyridylmethyl
- 4-pyridylmethyl -continued

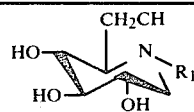

| $R_1$ |
|---|
| 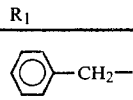 |

Compounds of the formula

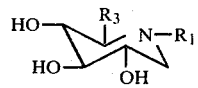

| $R_1$ | $R_3$ |
|---|---|
| H— | $CH_3$— |
| H— | $CH_3CH_2$— |
| H— | $CH_3CH_2CH_2$— |
| H— | $CH(CH_2)_6$—$CH_2$— |
| H— | $H_3C$—O—$CH_2$— |
| H— | $H_5C_2$—O—$CH_2$— |
| H— | $H_3C$—COO—$CH_2$— |
| H— | 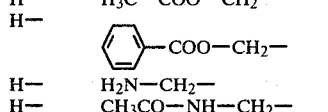—COO—$CH_2$— |
| H— | $H_2N$—$CH_2$— |
| H— | $CH_3CO$—NH—$CH_2$— |
| H— | 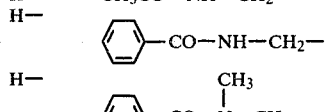—CO—NH—$CH_2$— |
| H— | 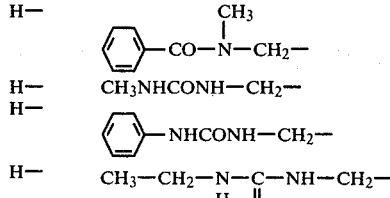—CO—N(CH$_3$)—$CH_2$— |
| H— | $CH_3NHCONH$—$CH_2$— |
| H— | 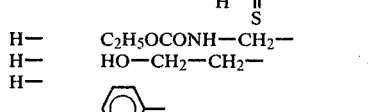—NHCONH—$CH_2$— |
| H— | $CH_3$—$CH_2$—NH—C(=S)—NH—$CH_2$— |
| H— | $C_2H_5OCONH$—$CH_2$— |
| H— | HO—$CH_2$—$CH_2$— |
| H— | 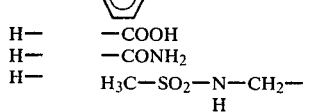 |
| H— | —COOH |
| H— | —$CONH_2$ |
| H— | $H_3C$—$SO_2$—NH—$CH_2$— |
| H— | $H_3C$—$H_2C$—$SO_2$—NH—$CH_2$— |
| H— | 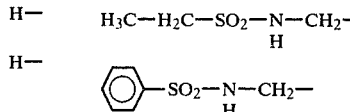—$SO_2$—NH—$CH_2$— |
| $CH_3$— | $CH_3$— |
| $CH_3$— | $CH_3CH_2$— |
| $CH_3$— | $CH_3CH_2CH_2$— |
| $CH_3$— | $CH_3(CH_2)_6$—$CH_2$— |
| $CH_3$— | $H_3C$—O—$CH_2$— |
| $CH_3$— | $H_5C_2$—O—$CH_2$— |
| $CH_3$— | $H_3C$—COO—$CH_2$— |
| $CH_3$— | 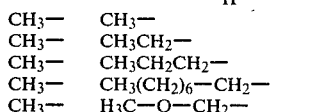—COO—$CH_2$— |
| $CH_3$— | $H_2N$—$CH_2$— |
| $CH_3$— | $CH_3CO$—NH—$CH_2$— |
| $CH_3$— | 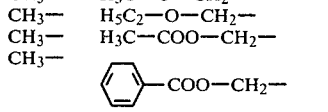—CO—NH—$CH_2$— |
| $CH_3$— | 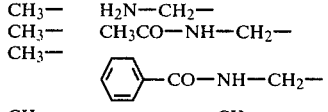—CO—N(CH$_3$)—$CH_2$— |
| $CH_3$— | $CH_3NHCONH$—$CH_2$— |

-continued

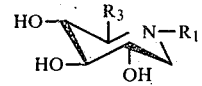

| $R_1$ | $R_3$ |
|---|---|
| $CH_3$— | 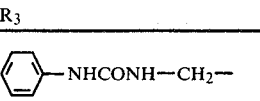—NHCONH—$CH_2$— |
| $CH_3$— | $CH_3$—$CH_2$—NH—C(=S)—NH—$CH_2$— |
| $CH_3$— | $C_2H_5OCONH$—$CH_2$— |
| $CH_3$— | HO—$CH_2$—$CH_2$— |
| $CH_3$— | 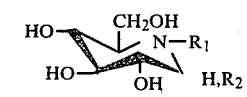 |
| $CH_3$— | —COOH |
| $CH_3$— | —$CONH_2$ |
| $CH_3$— | $H_3C$—$SO_2$—NH—$CH_2$— |
| $CH_3$— | $H_3C$—$H_2C$—$H_2C$—$SO_2$—NH—$CH_2$— |
| $CH_3$— | 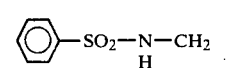—$SO_2$—NH—$CH_2$— |

Compounds of the formula

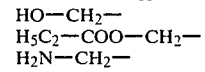

With respect to the configuration at the C-1 atom, the examples listed below include both the α-form and the β-form

| $R_1$ | $R_2$ |
|---|---|
| H— | $H_2N$—$CH_2$— |
| H— | $CH_3CO$—NH—$CH_2$— |
| H— | 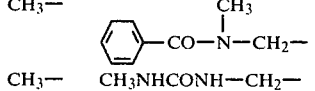—CO—NH—$CH_2$— |
| H— | 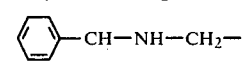—CO—N(CH$_3$)—$CH_2$— |
| H— | $CH_3NHCONH$—$CH_2$— |
| H— | 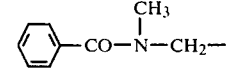—NHCONH—$CH_2$— |
| H— | $CH_3$—$CH_2$—NH—C(=S)—NH—$CH_2$— |
| H— | $C_2H_5OCONH$—$CH_2$— |
| H— | —COOH |
| H— | —$COOC_2H_5$— |
| H— | —$CONH_2$ |
| H— | $H_3C$—$SO_2$—NH—$CH_2$ |
| H | $H_3C$—$H_2C$—$H_2C$—$SO_2$—NH—$CH_2$— |
| H— | 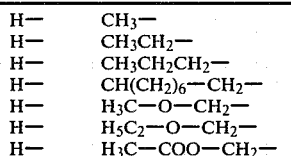—$SO_2$—NH—$CH_2$ |
| H— | HO—$CH_2$— |
| H— | $H_5C_2$—COO—$CH_2$— |
| $CH_3$— | $H_2N$—$CH_2$— |
| $CH_3$— | $CH_3CO$—$NHCH_2$— |
| $CH_3$— | —CH—NH—$CH_2$— |
| $CH_3$— | 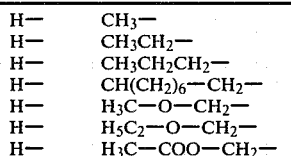—CO—N(CH$_3$)—$CH_2$— |

-continued

| R₁ | R₂ |
|---|---|
| CH₃— | CH₃NHCONH—CH₂— |
| CH₃— | —NHCONH—CH₂— |
| CH₃— | CH₃—CH₂—NH—C(=S)—NH—CH₂— |
| CH₃— | C₂H₅OCONH—CH₂— |
| CH₃— | —COOH |
| CH₃— | —COOC₂H₅ |
| CH₃— | —CONH₂ |
| CH₃— | H₃C—SO₂—NH—CH₂— |
| CH₃— | H₃C—H₂C—H₂C—SO₂—NH—CH₂— |
| CH₃— | —SO₂—NH—CH₂— |
| CH₃— | HO—CH₂— |
| CH₃— | H₅C₂—COO—CH₂— |
| CH₃— | —OH |
| CH₃— | —SO₃H |
| CH₃— | —CN |
| CH₃— | —OCH₃ |
| CH₃— | —O—CH₂—CH₂—CH₂—CH₃ |
| CH₃— | —SH |
| CH₃— | —S—CH₂—CH₃ |
| CH₃— | —NH₂ |
| CH₃— | —NH—CH₃ |

Compounds of the formula

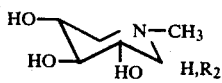

With respect to the configuration at the C-2 atom, the examples listed below include both the α-form and the β-form

| R₂ |
|---|
| H₂N—CH₂— |
| CH₃CO—NH—CH₂— |
| —CO—NH—CH₂— |
| —CO—N(CH₃)—CH₂— |
| CH₃NHCONH—CH₂— |
| —NHCONH—CH₂— |
| CH₃—CH₂—NH—C(=S)—NH—CH₂— |
| C₂H₅OCONH—CH₂— |
| —COOH |
| —COOC₂H₅ |
| —CONH₂ |
| H₃C—SO₂—NH—CH₂— |
| H₃C—H₂C—H₂C—SO₂—NH—CH₂— |
| —SO₂—NH—CH₂— |
| HO—CH₂— |
| H₅C₂—C(=O)—O—CH₂— |
| —OH |
| —CN |
| —SO₃H |
| —OCH₃ |
| —O—CH₂—CH₂—CH₂—CH₃ |
| —SH |
| —S—CH₂—CH₃ |
| —NH₂ |
| —NH—CH₃ |

Compounds of the formula

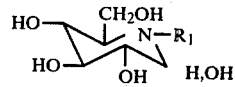

| R₁ |
|---|
| —CH₂—CH₃ |
| —CH₂—CH₂—CH₂—CH₃ |
| —CH₂—(CH₂)₁₆—CH₃ |
| —CH(CH₃)₂ |
| —CH₂— |
| —CH₂—CH=CH₂— |
| —CH₂—CH₂—OCH₃— |
| —CH₂—CH₂—N(CH₃)₂ |
| —CH₂—(HO) |

Compounds of the formula

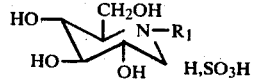

| R₁ |
|---|
| —CH₂—CH₃ |
| —CH₂—CH₂—CH₂—CH₃ |
| —CH₂—(CH₂)₁₆—CH₃ |
| —CH(CH₃)₂ |
| —CH₂— |
| —CH₂—CH=CH₂ |
| —CH₂—CH₂—OCH₃ |
| —CH₂—CH₂—N(CH₃)₂ |
| —CH₂—(HO) |

Compounds of the formula

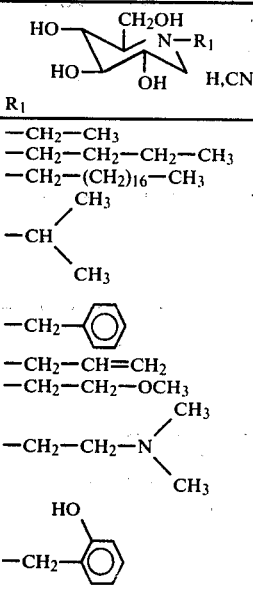

| $R_1$ |
|---|
| —CH$_2$—CH$_3$ |
| —CH$_2$—CH$_2$—CH$_2$—CH$_3$ |
| —CH$_2$—(CH$_2$)$_{16}$—CH$_3$ |
| —CH(CH$_3$)$_2$ |
| —CH$_2$—C$_6$H$_5$ |
| —CH$_2$—CH=CH$_2$ |
| —CH$_2$—CH$_2$—OCH$_3$ |
| —CH$_2$—CH$_2$—N(CH$_3$)$_2$ |
| —CH$_2$—(4-HO-C$_6$H$_4$) |

The inhibitors according to the invention are suitable for use as therapeutic agents for the following indications: prediabetes, gastritis, constipation, infections of the gastro intestinal tract, meteorismus, flatulence, caries, atherosclerosis, hypertension and in particular obesity, diabetes and hyperlipoproteinaemia. To broaden the activity spectrum, it is possible to combine inhibitors for glycoside-hydrolases which complement one another in their action, the combinations being either combinations of two or more compounds according to the invention with one another or combinations of the compounds according to the invention with inhibitors which are already known. Thus, for example, it can be appropriate to combine saccharase inhibitor compounds according to the invention with amylase inhibitors which are already known.

In some cases, combinations of the compounds according to the invention with known oral antidiabetic agents ($\beta$-cytotropic sulphonylurea derivatives and/or biguanides having an action on the blood sugar) and with blood lipid-lowering active compounds, such as, for example, clofibrate, nicotinic acid, cholestyramine and others, are advantageous.

The compounds can be administered without dilution, for example as a powder or in a gelatine casing, or in combination with an excipient in a pharmaceutical composition.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose, or for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. C$_{14}$-alcohol with C$_{16}$-fatty acid]) or mixtures of these diluents.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface active agents (e.g. ethoxylated isostearyl alcohols, polyoxyethylene sorbite and sorbitane esters), microcrystalline cellulose, aluminium metahydroxide, bentonite, agar-agar and tragecanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragrees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 500 to $5 \times 10^6$ SIU (as defined hereinbelow) or from 1 to 3500 mg, most preferably from 10 to 500 mg active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously or introvenously), rectally or locally, preferably orally. Preferred pharmaceutical compositions and medicaments are therefore those adapted for oral administration, such as tablets, capsules, powders, dragees, granules, suspensions and solutions. Administration in the method of the invention is preferably orally.

In general it has proved advantageous to administer amounts of from 10 to $1 \times 10^4$ SIU (as defined hereinbelow) or amounts of from 0.01 mg to 100 mg, preferably from 0.1 to 10 mg, per kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

In addition to the above mentioned pharmaceutical compositions, foodstuffs containing these active compounds can also be prepared; for example sugar, bread, potato products, fruit juices, beer, chocolate and other confectionery, and preserves, such as, for example, jam, a therapeutically active amount of at least one of the inhibitors according to the invention having been added to these products.

The food products produced using the active compounds according to the invention are suitable for use both in the diet of patients suffering from metabolic disorders and for the nutrition of healthy persons in the sense of a method of nutrition for the prophylaxis of metabolic disorders.

Furthermore, the inhibitors according to the invention have the property, in animals, of influencing to a high degree the ratio of the proportion of undesired fat to the proportion of desired meat of low fat content (lean meat) in favour of the lean meat. This is of particular importance for the rearing and keeping of agricultural stock animals, for examle in the fattening of pigs, but is also of considerable importance for the rearing and keeping of other stock animals and pets. Furthermore, the use of the inhibitors can lead to a considerable rationalisation of the feeding of the animals, both in respect of time, quantity and quality. Since they cause a certain delay in digestion, the residence time of the nutrients in the digestive tract is extended, whereby ad libitum feeding associated with less expense is made possible. Furthermore, in many cases there is a considerable saving of valuable protein feed when the inhibitors according to the invention are used.

The active compounds can thus be used in virtually all spheres of animal nutrition as agents for reducing the formation of fatty layers and for the conservation of feed protein.

The activity of the active compounds here is essentially independent of the nature and the sex of the animals. The active compounds prove particularly valuable in species of animals which tend generally to deposit relatively large amounts of fat, or tend to do so during certain stages of their life.

The following stock animals and pets may be mentioned as examples of animals for which the inhibitors for reducing the formation of fatty layers and/or for conserving feed protein can be employed: warm-blooded animals, such as cattle, pigs, horses, sheep, goats, cats, dogs, rabbits, fur-bearing animals, for example mink and chinchillas, and other pets, for example guineapigs and hamsters, laboratory animals and zoo animals, for example rats, mice, monkeys and the like, poultry, for example broilers, chickens, geese, ducks, turkeys and pigeons, parrots and canaries, and cold-blooded animals, such as fish, for example carp, and reptiles, for example snakes.

Because of the advantageous properties of the active compounds of the invention, the amount of active compound administered to the animals in order to achieve the desired effect can be varied within broad limits. It is preferably from 0.1 to 1000 mg most preferably from 1.0 to 100 mg/kg of feed per day. The period over which the active compound is administered can be from a few hours or days to several years. The appropriate amount of active compound and the appropriate period over which it is administered are closely connected with the object of feeding. In particular, they depend on the nature, the age, the sex and the state of health and the method of keeping the animals and can be easily determined by any expert.

The active compounds according to the invention may be administered to the animal by customary methods. The nature of the administration route depends, in particular, on the nature, the behaviour and the general condition of the animals. Thus it is possible to carry out the administration orally once or several times daily, at regular or irregular intervals. In most cases, oral administration, in particular in synchromism with the food and/or drink intake of the animals, is to be preferred for reasons of expediency.

The active compounds of the invention may be administered as pure substances or in a formulated form, the expression "formulated form" including both a premix for admixture with the animal feed or drinking water, that is to say mixed with a non-toxic inert carrier of any desired nature, and also as part of a total ration in the form of a supplementary feed and as a constituent of the mixture of a mixed feed by itself. Administration of suitable formulations by means of the animal drinking water is also included.

The active compounds according to the invention, optionally in the formulated form, can also be administered, in a suitable form, together with other nutrients and active compounds, for example mineral salts, trace elements, vitamins, proteins, energy carriers (for example starch, sugar or fats), dyestuffs and/or flavouring substances or other feedstuff additives, such as, for example, growth promoters. The active compounds of the invention can be administered to the animals before, during or after their food intake.

Oral administration together with the feed and/or drinking water is advisable, the active compounds being added to the total amount or only to certain parts of the feed and/or drinking water, depending on the requirement.

The active compounds of the invention can be added to the feed and/or the drinking water according to customary methods by simple admixture of the pure compound, preferably in a finely divided form, or in a formulated form mixed with edible, non-toxic carriers, and optionally also in the form of a premix or a feed concentrate.

The feed and/or drinking water can, for example, contain the active compounds according to the invention in a concentration of from 0.001° to 5.0°/oo, most preferably from 0.01° to 2.0°/oo (by weight). The optimum level of the concentration of the active compound in the feed and/or drinking water depends, in particular, on the size of the feed and/or drinking water intake of the animals and can be easily determined by any person skilled in the art.

The nature of the feed itself and its composition does not normally influence the utilisation of the compounds of the invention. Thus it is possible to use all the current, commercially available or special feed compositions, which preferably contain the customary proportions of energy substances and proteins, including vitamins and mineral substances, necessary for balanced nutrition. The feed can be composed, for example, of vegetable substances, for example shredded oil-cake, shredded cereal and cereal by-products, but also of hay, silage fodder, beets, and other forage plants, of animal substances, for example meat and fish products, bonemeal, fats and vitamins, for example A, D, E, K and B-complex, as well as special sources of protein, for example yeasts and certain aminoacids, and mineral substances and trace elements, such as, for example, phosphorus and iron, zinc, manganese, copper, cobalt, iodine and the like.

Premixes can preferably contain from 0.1 to 50%, most preferably from 0.5 to 5.0% (by weight) of, for example, N-methyl-1-desoxynorjirimycin, in addition to any desired edible carrier and/or mineral salt, for example carbonated feed lime, and may be prepared by customary mixing methods.

Mixed feeds preferably contain from 0.001° to 5.0°/oo, in particular from 0.02° to 2.0°/oo (by weight), for example, of N-methyl-1-desoxynorjirimycin, in addition to the customary raw material components of a mixed feed, for example shredded cereal or cereal by-products, shredded oilcake, animal protein, minerals, trace elements and vitamins. They can be prepared by customary mixing methods.

The active compounds of the invention when in premixes and mixed feedstuffs can preferably also be appropriately protected from air, light and/or moisture by suitable agents which cover their surface, for example with non-toxic waxes or gelatine.

The following is an example of a composition of a finished mixed feed, for poultry, containing an active compound according to the invention: 200 g of wheat, 340 g of maize, 360.3 g of coarse soya beam meal, 60 g of beef tallow, 15 g of dicalcium phosphate, 10 g of calcium carbonate, 4 g of iodinated sodium chloride, 7.5 g of a vitamin/mineral mixture and 3.2 g of an active compound premix yielding, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 meg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$. The active compound premix contains, for example, N-methyl-1-desoxynojirimycin in the desired amount, for example 1,600 mg, and in addition 1 g of DL-methionine and enough soya bean flour to form 3.2 g of premix.

The following is an example of the composition of a mixed feed for pigs, which feed contains an active compound of the formula I: 630 g of shredded cereal feed (composed of 200 g of shredded maize, 150 g of shredded barley, 150 g of shredded oats and 130 g of shredded wheat), 80 g of fishmeal, 60 g of coarse soya bean meal, 58.8 g of tapioca flour, 38 g of brewer's yeast, 50 g of a vitamin/mineral mixture for pigs (constitution for example, as in the chicken feed above), 30 g of linseed cake meal, 30 g of maize gluten feed, 10 g of soya bean oil, 10 g of cane sugar molasses and 2 g of active compound premix (constitution for example, as in the chicken feed above) yield, after careful mixing, 1 kg of feed.

The feed mixtures indicated are intended, preferably, for the rearing and fattening of chickens or pigs respectively; however, they can also be used in identical or similar compositions for the rearing and fattening of other animals.

The compounds of the invention can be used individually or in any desired mixture with one another.

In vitro saccharase inhibition test

The in vitro saccharase inhibition test makes it possible to determine the enzyme-inhibitory activity of a substance by comparison of the activity of the solubilised intestinal disaccharidase complex in the presence and in the absence (so-called 100% value) of the inhibitor (compound under scrutiny). A virtually glucose-free sucrose (glucose < 100 ppm) is used here as the substrate which determines the specificity of the inhibition test; the determination of enzyme activity is based on the spectrophotometric determination of glucose liberated, using glucose dehydrogenase and nicotinamide-adenine dinucleotide as the cofactor.

One saccharase inhibitior unit (SIU) is defined as that inhibitory activity which, in a defined test batch, reduces a given saccharolytic activity by one unit (saccharase unit=SU); the saccharase unit being defined here as that enzyme activity which splits off one $\mu$mol of sucrose per minute under given conditions and thus leads to the liberation of one $\mu$mole each of glucose, which is determined in the test, and fructose, which is not recorded in the test.

The intestinal disaccharidase complex is obtained from swine small intestine mucosa by tryptic digestion, precipitation from 66% strength ethanol at $-20°$ C., taking up of the precipitate in 100 mM phosphate buffer, pH 7.0, and finally dialysis against the same buffer.

100 $\mu$l of a dilution of the intestinal disaccharidase complex in 0.1 M maleate buffer, pH 6.25, are added to 10 $\mu$l of a sample solution, which is prepared so that the extinction of the test batch is at least 10%, but not more than 25%, below that of the 100% value, and the mixture is pre-incubated at 37° C. for 10 minutes. The dilution of the disaccharidase complex should normally be adjusted to an activity of 0.1 SU/ml.

The saccharolytic reaction is started by adding 100 $\mu$l of a 0.4 M solution of source ("Serva 35579") in 0.1 M maleate buffer, pH 6.25, and, after an incubation period of 20 minutes at 37° C., is stopped by adding 1 ml of glucose dehydrogenase reagent (1 small bottle of lyophilised glucose dehydrogenase/mutarotase mixture ("Merck 14053") and 331.7 mg of $\beta$-nicotinamide-adenine dinucleotide (free acid "BOEHRINGER" degree of purity I) dissolved in 250 ml of 0.5 M tris buffer, pH 7.6). In order to determine the glucose concentration, the mixture is incubated at 37° C. for 30 minutes and finally is measured photometrically at 340 nm against a reagent blank (containing enzyme but without sucrose).

The calculation of the inhibitory activity of inhibitors is made difficult by the fact that even slight changes in the test system, for example a 100% value which varies slightly from determination to determination, can have a significant effect on the test result which cannot be ignored. These difficulties may be avoided by running a standard with every determination; a saccharase inhibitor of the formula $C_{25}H_{43}O_{18}N$ which has a specific inhibitory activity of 77,700 SIU/g and, when employed in the test in amounts of 10 to 20 ng, leads to an inhibition of the order of size specified above, is conveniently used as the standard. If the difference between the extinctions at 340 nm of the 100% value and of the batch inhibited by the standard is known, the specific inhibitory activity of the inhibitor, expressed in saccharase inhibitor units per gram (SIU/g), can be calculated in a known manner from the extinction difference between the 100% value and the batch inhibited by the sample solution, taking into consideration the amount of inhibitor employed.

| Specific saccharase-inhibitory activity in vitro | |
|---|---|
| 1-Desoxynojirimycin | 465,000 SIU/g |
| N-Methyl-1-desoxynojirimycin | 2,330,000 SIU/g |

PREPARATION EXAMPLES

Example 1

N-Methyl-1-desoxynojirimycin

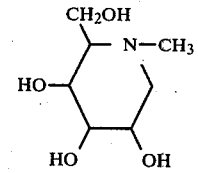

3.2 g of 1-desoxynojirimycin and 2 ml of 30% strength aqueous formaldehyde are added to 4 ml of 98% strength formic acid, whilst cooling with ice. The mixture is then heated under reflux for 8 hours. After cooling, the reaction mixture is diluted with acetone. A resinous precipitate separates out. The acetone solution is decanted off and the resin is rinsed several times with acetone. The residue is then dissolved in distilled water and the solution is freed from formic acid by adding a basic ion exchanger in the $^\ominus$OH form (Amberlite JRA 410). The ion exchanger is filtered off and the aqueous solution is brought to dryness under reduced pressure. 3.0 g of resinous N-methyl-1-desoxynojirimycin remain. The compound can be further purified by chromatography on cellulose. Water-containing butanol is used as the running agent. The compound may be crystallized from ethanol. M.P.: 153° C.

Mass spectrum: The most important peak in the upper mass range is at m/e=146 (M—CH$_2$OH).

For further characterisation, the compound is converted into the peracetylated compound, N-methyl-2,3,4,6-tetra-O-acetyl-1-desoxynojirimycin, with acetic anhydride/pyridine 1:1 at room temperature. A proton magnetic resonance spectrum of this derivative in CDCl$_3$ was measured at 100 MHz: 4 singlets for the total of 12 protons, which correspond to the methyl groups of the O-acetyl groups

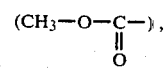

are found between $\delta=2.0$ and 2.1 ppm. The methyl group bonded to N(C$\underline{H}_3$—N<) is found as a singlet at δ=2.45 ppm. Two protons on a C atom bonded to nitrogen

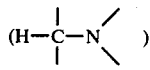

absorb as poorly resolved multiplets between δ=2.1 and 2.5 ppm. A further proton of this type appears as a doublet of a doublet ($J_1=11$ Hz; $J_2=4$ Hz) at δ=3.18 ppm. A methylene group

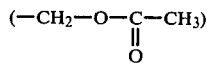

absorbs as an AB system at δ=4.16 and δ=4.22 ppm. The remaining three protons

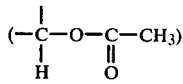

are found as a multiplet between =4.9 and 5.2 ppm.

Example 2

N-n-Butyl-1-desoxynojirimycin

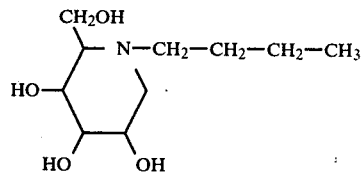

12.5 ml of n-butyraldehyde, 0.01 mols of methanolic HCl and 1.5 g of NaCNBH$_3$ are added successively to 3.2 g of 1-desoxynojirimycin (0.02 mol) in 40 ml of absolute methanol, whilst cooling with ice and stirring. The reaction mixture is stirred at room temperature for 12 hours. It is then concentrated to dryness on a rotary evaporator. The residue is dissolved in 50 ml of water and extracted 3 times with 30 ml of CHCl$_3$ each time. The aqueous phase is again brought to dryness, the residue is taken up in 30 ml of H$_2$O and the solution is discharged onto a column 50 cm long and 2 cm wide which is filled with a strongly basic ion exchange resin in the OH$^\ominus$ form (Amberlite IRA 400 or Dowex 1×2).

The reaction product is eluted with water and the individual fractions are investigated by thin layer chromatography. (Silica gel plates; running agent: ethyl acetate/methanol/water/25% strength ammonia 100:60:40:2; spray reagent: KMnO$_4$ solution). The fractions which contain N-n-butyl-1-desoxynojirimycin are collected and the aqueous solution is concentrated on a rotary evaporator. Acetone is added to the residue, whereupon crystallisation occurs.

The crystals are filtered off, rinsed briefly with acetone and dried. 3 g of N-n-butyl-1-desoxynojirimycin of melting point 126°–127° C. are obtained.

Mass spectrum: The most important peaks in the upper mass range are found at m/e=188 (M—CH$_2$OH) and m/e=176 (M—CH$_2$—CH$_2$—CH$_3$).

In the case of less reactive aldehydes, a molecular sieve 3 Å was added to the reaction mixture in order to bind the water of reaction.

The following compounds were prepared by methods analogous to those of the above procedure:

N-Ethyl-1-desoxynojirimycin

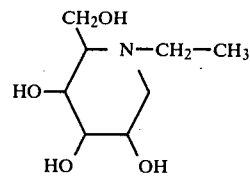

Mass spectrum: Intense peak at m/e=160 (M—CH$_2$OH).

N-n-Propyl-1-desoxynojirimycin

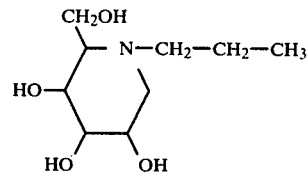

Mass spectrum: Intense peak at m/e=174 (M—CH$_2$OH). Peaks also at m/e=206 (M+H) and m/e=204 (M—H).

N-iso-Butyl-1-desoxynojirimycin

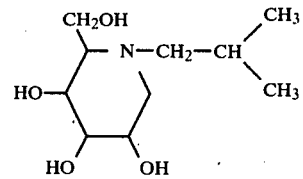

Mass spectrum: The most important peaks in the upper mass range are found at m/e=188 (M—CH$_2$OH), m/e=176

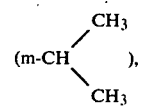

m/e=220 (M+H) and m/e=218 (M—H).

N-n-Heptyl-1-desoxynojirimycin

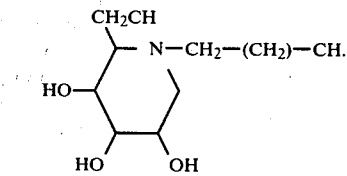

melting point: 111°–113° C. (from aceton)

Mass spectrum: The most important peak in the upper mass range is at m/e=230 (M—CH$_2$OH). Peaks are also found at m/e=262 (M+H) and 260 (M—H).

N-Benzyl-1-desoxynojirimycin

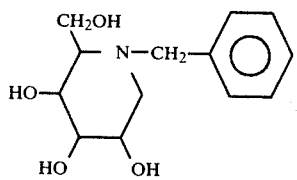

melting point: 183°–184° C. (from methanol)

Mass spectrum: The most important peak in the upper mass range is found at m/e=222 (M—CH$_2$OH).

N-(2-Pyridyl)-methyl-1-desoxynojirimycin

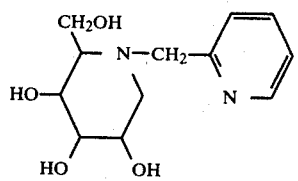

melting point: 174°–175° C. (from ethanol)

Mass spectrum: The most important peaks in the upper mass range are found at m/e=255 (M+H), m/e=236 (M—H$_2$O) and m/e=223 (M—CH$_2$OH).

N-2-Hydroxyethyl-1-desoxynojirimycin

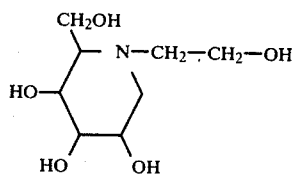

melting point: 114° C. (from ethanol)

Mass spectrum: The most important peak in the upper mass range is at m/e=176 (M—CH$_2$OH).

N-2,3-Dihydroxy-n-propyl-1-desoxynojirimycin

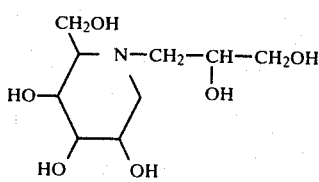

Mass spectrum: The most important peaks in the upper mass range are at m/e=206 (M—CH$_2$OH) and m/e=176. The substance is a mixture of two diastereomeric compounds.

N-(S-β-D-Glucopyranosyl-2-mercaptoethyl)-1-desoxynojirimycin

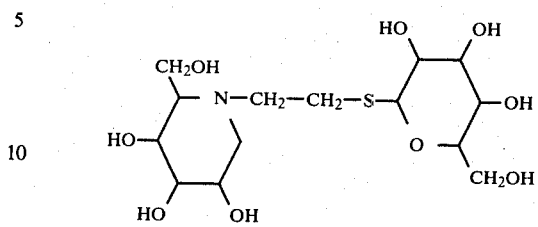

Mass spectrum: The mass spectrum of the compound peracetylated in pyridine/acetic anhydride was measured. The most important peaks in the upper mass range are found at m/e=648

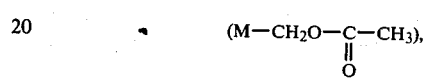

m/e=588 and m/e=344.

The aldehyde required for the reaction was obtained from O-acetylated 1-thioglucose and chloroacetaldehyde. The acetyl groups in the end product were split off by transesterification with catalytic amounts of NaOCH$_3$ in MeOH.

N-Oxiranyl-methyl-1-desoxynojirimycin

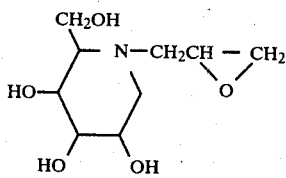

Mass spectrum: The most important peaks in the upper mass range are found at m/e=219 (M), m/e=202, m/e=188 (M—CH$_2$OH) and m/e=176

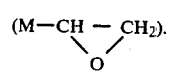

The substance is a mixture of two diastereomeric compounds.

N-(3-N-Phthalimido-n-propyl)-1-desoxynojirimycin

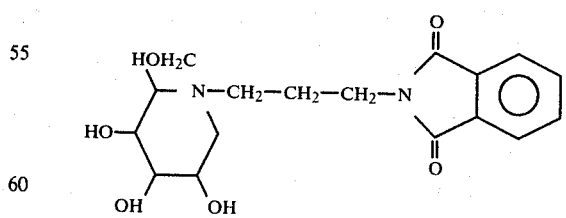

Mass spectrum: The most important peaks in the upper mass range were found at m/e=348, m/e=319 (M—CH$_2$OH), m/e=301, m/e=200, m/e=188, m/e=174, m/e=160 and m/e=147.

In this case, chromatography on a basic ion exchange resin was dispensed with and the compound was purified by boiling up with acetone and recrystallisation from ethanol.

Melting point: 208°–210° C.

N-(3-Amino-n-propyl)-1-desoxynojirimycin

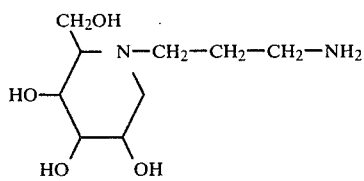

Mass spectrum: The most important peaks in the upper mass range are at m/e=189 (M—CH₂OH) and m/e=146.

The compound was obtained from the above phthalimido compound by hydrazinolysis in methanol.

N-(1-Desoxynojirimycin-yl)-acetic acid

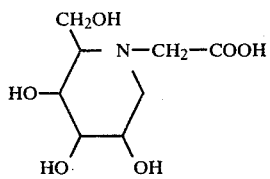

Mass spectrum: The most important peaks in the upper mass range are found at m/e=203 (M—H₂O), m/e=159, m/e=145 and m/e=100.

The compound was not purified by chromatography over a basic ion exchange resin but by recrystallisation from methanol/water.

Melting point: 187°–188° C.

N-o-Nitrobenzyl-1-desoxynojirimycin

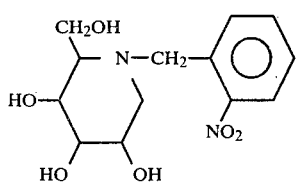

Rf value: 0.85 (on thin layer chromatography ready-to-use silica gel 60 plates from Messrs. Merck; running agent: ethyl acetate/methanol/H₂O/25% strength ammonia 100:60:40:2). For comparison: RF value of 1-desoxynojirimycin: 0.3.

N-o-Carboxybenzyl-1-desoxynojirimycin

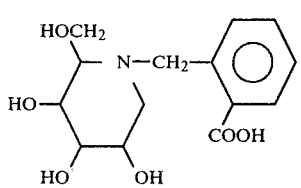

Rf value: 0.7 (plates and running agent is indicated for the above compound).

For purification, the compound was chromatographed over a basic ion exchange resin as indicated above, but finally was eluted with 1% strength acetic acid.

N-p-Carboxybenzyl-1-desoxynojirimycin

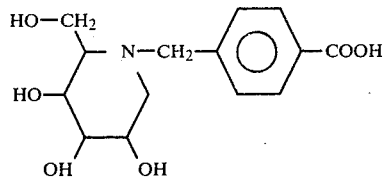

m.p.: 280°–281° C. (from H₂O/methanol)

Rf value: 0.7 (plates and running agent as indicated above).

In this case also, the compound was eluted from the basic ion exchange resin with 1% strength acetic acid.

N-p-Sulfobenzyl-1-desoxynojirimycin

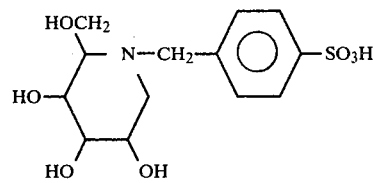

4.8 g of benzaldehyd-4-sulfonic acid, 1.8 ml of acetic acid and 0.8 g of NaCNBH₃ are added to 2 g of 1-desoxy-nojirimycin in 40 ml methanol. The mixture was refluxed for 4 hours and stirred for 12 hours at room temperature. The precipitate was filtered off and recrystallized from water. 1.2 g of N-p-sulfobenzyl-1-desoxynojirimycin of melting point ~320° C. (dec.) are obtained.

Example 3

N-β-Phenylethyl-1-desoxynojirimycin

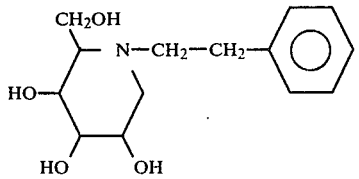

3 g of phenylacetaldehyd and 0.8 g of NaCNBH₃ are added to 2 g of 1-desoxynojirimycin and 1.8 ml acetic acid in 40 ml of methanol. The mixture is stirred for 12 hours at room temperature and evaporated on a rotary evaporator. The residue is dissolved in ethanol/water (2:1) and discharged onto a column which is filled with a strongly acidic ion exchange resin in the H⊕-form. The column is washed with 2 l of ethanol and water (2:1). Then the product is eluted with ethanol/2% strength aqueous ammonia (2:1). The fractions are investigated by thin layer chromatography and those which contain the product are collected and dried. The residue is crystallized from 100 ml ethanol. 2.5 g of N-3-phenyl-ethyl-1-desoxynojirimycin with a melting point 179°–181° C. are obtained.

The following compounds were prepared analogously: N-n-Pentyl-1-desoxynojirimycin

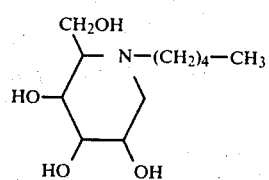

m.p. 97° C. (from acetone)

N-n-Hexyl-1-desoxynojirimycin

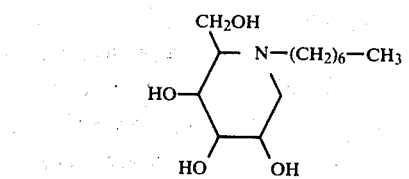

m.p. 112°–113° C. (from ethanol/acetone)

N-n-Octyl-1-desoxynojirimycin

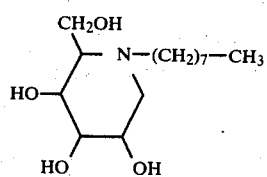

m.p. 115°–117° C. (from ethanol/acetone)

N-n-Nonyl-1-desoxynojirimycin

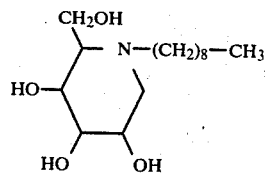

m.p. 105°–107° C. (from ethanol/acetone)

N-n-Decyl-1-desoxynojirimycin

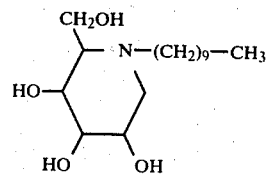

m.p. 151° C. (sinters at 91° C. from MeOH/acetone)

N-n-Undecyl-1-desoxynojirimycin

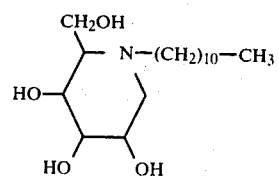

m.p. 162° C. (sinters at 91° C. from ethanol/acetone)

N-n-Dodecyl-1-desoxynojirimycin

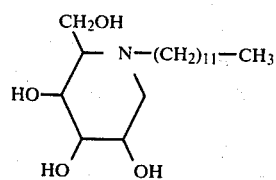

m.p. 164° C. (sinters at 97° C. from ethanol/acetone)

N-n-Tetradecyl-1-desoxynojirimycin

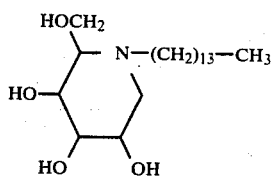

m.p. 105°–107° C. (from methanol)

N-n(5'-Hydroxypentyl)-1-desoxynojirimycin

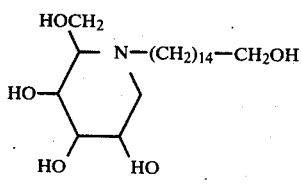

m.p. 86°–87° C. (from butanol)

N-Cyclohexylmethyl-1-desoxynojirimycin

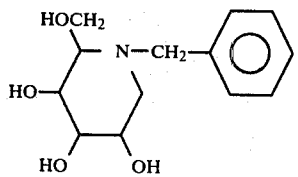

m.p. 138°–140° C. (from acetone)

N-(3'-Cyclohexenylmethyl)-1-desoxynojirimycin

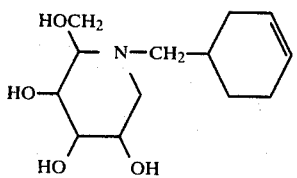

m.p. 142°–144° C. (from acetone)

N-(2'-Norbornen-5'-yl-methyl)-1-desoxynojirimycin

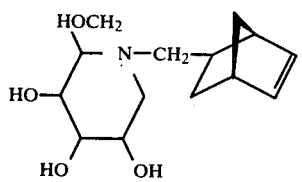

m.p. 160°–162° C. (from ethanol)

N-p-Chlorbenzyl-1-desoxynojirimycin

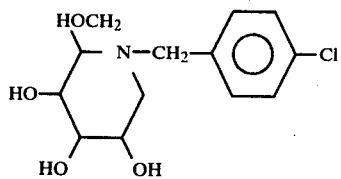

m.p. 153°–155° C. (from acetone)

N-m-Methylbenzyl-1-desoxynojirimycin

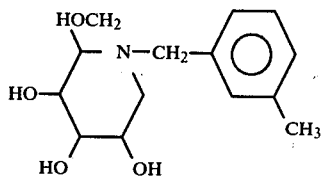

m.p. 134°–136° V. (from methanol)

N-(p-Biphenylmethyl)-1-desoxynojirimycin

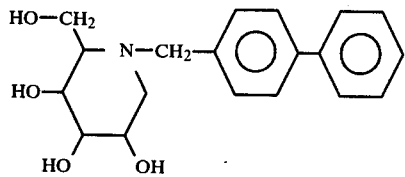

m.p. 240°–245° C. (from water/ethanol)

N-(n-3'-phenylpropyl)-1-desoxynojirimycin

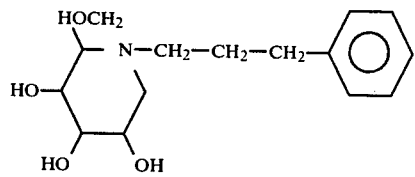

m.p. 125°–127° C. (from ethanol)

Example 4

N-Allyl-1-desoxynojirimycin

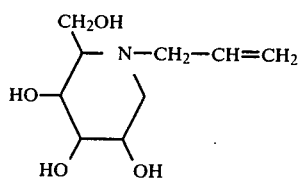

5 g of 1-desoxynojirimycin, 5 g of Ag$_2$O and 5 g of Allylbromide are stirred in 30 ml of dimethylformamide and 30 ml of water for 3 hours at room temperature. The silver salts are filtered off and the filtrate is evaporated at the rotary evaporator. The residue is recrystallized from ethanol. 4.5 g of N-allyl-1-desoxynojirimycin of melting point 131° to 132° C. are obtained.

The following products are obtained analogously, the isolation and purification optionally carried out by chromatography on a strongly acidic ion exchange resin (H$^\oplus$-form).

N-Propargyl-1-desoxynojirimycin

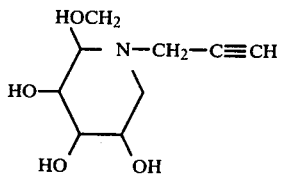

m.p. 160° C. (from acetone)

N-(3',4'-Dichlorbenzyl)-1-desoxynojirimycin

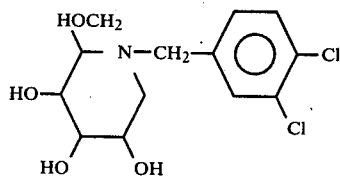

m.p. 130°–132° C.

N-(p-Nitrobenzyl)-1-desoxynojirimycin

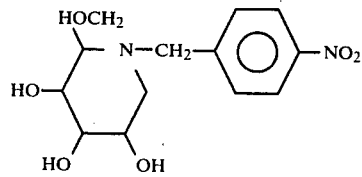

m.p. 144°–146° C.

N-(m-Nitrobenzyl)-1-desoxynojirimycin

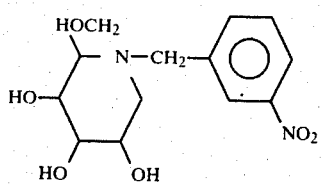

m.p. 168°–170° C.

Example 5

1-Cyano-1-desoxynojirimycin

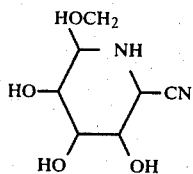

17.5 g of nojirimycin bisulfite adduct are added to 200 ml of water and 21.2 of Ba(OH)$_2$.8 H$_2$O. The mixture is stirred for 1 hour and the solid is filtered off. 12 ml of liquid HCN are added to the filtrate and the mixture is stirred for 30 minutes. The solution is filtered and concentrated on the rotary evaporator to 20 ml. 20 ml of methanol are added whereby the crystallization of the product starts. 100 ml of ethanol are added to complete crystallization. After filtration 12.0 g of 1-cyano-1-desoxynojirimycin are obtained m.p. 155°–156° C. (from methanol/water).

Example 6

N-Methyl-1-cyano-1-desoxynojirimycin

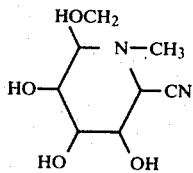

The compound is obtained from 1-cyano-1-desoxynojirimycin with 35% strength aqueous formaldehyd solution and NaCNBH$_3$ in methanol according to Example 3.

Mass spectrum: The most important peaks in the upper mass range are at m/e=171 (M—CH$_2$OH), m/e=157 and m/e=144.

Example 7

1-Desoxynojirimycin-1-carboxylic acid

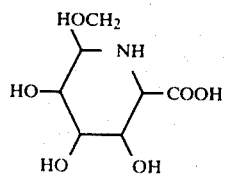

10 g of 1-cyano-1-desoxynojirimycin are refluxed with 5 g of sodium hydroxide in 100 ml of water for one hour. Hydrochloric acid is added up to pH 4. The mixture is dried on the rotary evaporator and the residue is extracted with hot methanol, sodium chloride is separated and the methanolic solution is evaporated. The residue is recrystallized from water and water/methanol. 10.5 g of 1-desoxynojirimycin-1-carboxylic acid of m.p. 268°–270° C. are obtained.

Example 8

1-Desoxynojirimycin-1-carboxylic acid ethyl ester

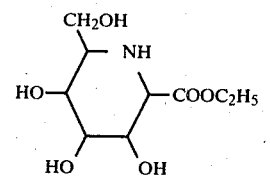

7 g of 1-desoxynojirimycin-1-carboxylic acid are refluxed with 100 ml of ethanolic hydrochloric acid for 2 hours and evaporated at the rotary evaporator. The residue is treated with ethanol and ethanolic ammonia. The solution was filtered and concentrated. 8 g of 1-desoxynojirimycin-1-carboxylic acid ethyl ester are obtained. NHR-Spectrum 100 MHz:

triplet at δ=1.3 ppm (3H, —COO—CH$_2$—CH$_3$);
multiplet at δ=2.4–2.6 ppm (1H,

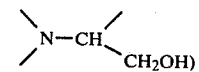

multiplet at δ=3.2–3.5 ppm (4H);
multiplet at δ=2.6–3.9 ppm (2H, —CH$_2$—OH);
quartet at δ=4.25 ppm (2H, —COO—CH$_2$—CH$_3$).

Example 9

N-Methyl-1-desoxynojirimycin-1-carboxylic acid ethylester

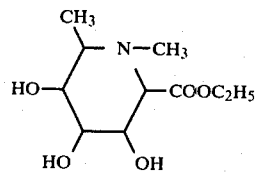

From 1-desoxynojirimycin-1-carboxylic acid ethyl ester according to example 6.

Mass spectrum: The most important peaks in the upper mass range are at m/e=218 (M—CH$_2$OH), m/e=200, m/e=176, m/e=158 and m/e=126.

Example 10

1-Desoxynojirimycin-1-carboxylic acid amide

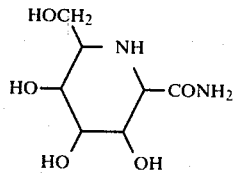

6 g of 1-desoxynojirimycin-1-carboxylic acid ethyl ester are refluxed in 90 ml of 25% strength aqueous ammonia for one hour. After cooling to room-temperature the solution is treated with ethanol and the precipitate (ammonium salt of 1-desoxynojirimycin-1-carboxylic acid) is separated off. The filtrate is concentrated, treated with water and chromatographed with a column filled with a strongly basic ion exchange resin (OH⊖-form). The product is eluted with water. The fractions containing the carbonamide are collected and concentrated. The residue is recrystallized from ethanol and 3 g of 1-desoxynojirimycin-1-carboxylic acid amide, m.p. 175°–176° C., are obtained.

Example 11

1-Desoxynojirimycin-1-carboxylic acid benzylamide

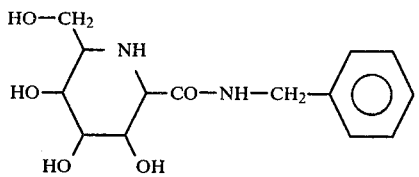

500 mg of 1-desoxynojirimycin-1-carboxylic acid ethyl ester are refluxed for 5 minutes in 1 ml of benzylamine. The mixture after cooling is treated several times with ether and the solvent decanted off. The residue is recrystallized from methanol and 400 mg of 1-desoxynojirimycin-1-carboxylic acid benzylamide, m.p. 221°–222° C. are obtained.

Example 12

N-Methyl-1-desoxynojirimycin-1-carboxylic benzyl amide

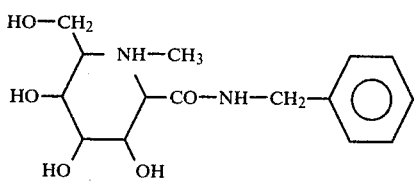

From 1-desoxynojirimycin-1-carboxylic acid benzylamide according to example 6; m.p. 229°–230° C. (from methanol).

Example 13

1-Aminomethyl-1-desoxynojirimycin

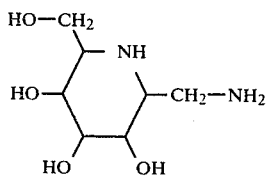

5 g of 1-cyano-1-desoxynojirimycin are hydrogenated in 100 ml of water with 10 g of Raney-Nickel and a pressure of 3.5 bar hydrogen. The catalyst is filtered off and the solution is dried on the rotary evaporator. The residue is treated with some hot methanol, filtered and evaporated. The residue is recrystallized from methanol to yield 3.4 g of 1-aminomethyl-1-desoxynojirimycin, m.p. 154°–155° C.

Example 14

1-Acetamidomethyl-1-desoxynojirimycin

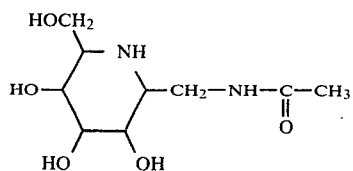

3.8 g of 1-aminomethyl-1-desoxynojirimycin in 40 ml methanol/water (1:1) are treated at 0° C. with 3 ml of acetic acid anhydride and stirred for 15 minutes at 0° C. and 30 minutes at room temperature. The solution was evaporated. The residue is treated with 60 ml of water and neutralized with a basic ion exchange resin (OH⊖-form). After removal of the resin the solution is dried and recrystallized twice from ethanol. 3 g of 1-acetamidomethyl-1-desoxynojirimycin are obtained, m.p. 169°–171° C.

Example 15

N-Methyl-1-acetamidomethyl-1-desoxynojirimycin

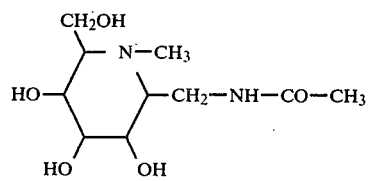

the compound is prepared from 1-acetamido-methyl-1-desoxynojirimycin analogously to example 6.

Mass spectrum: the most important peaks in the upper mass range are at m/e=176 and m/e=158.

Example 16

1-Benzoylaminomethyl-1-desoxynojirimycin

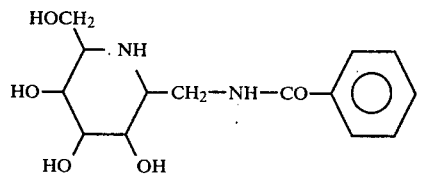

the compound is prepared from 1-aminomethyl-1-desoxynojirimycin and benzoylchloride according to example 14; m.p. 216° C. (from methanol).

Example 17

N-Methyl-1-benzoylamino-1-desoxynojirimycin

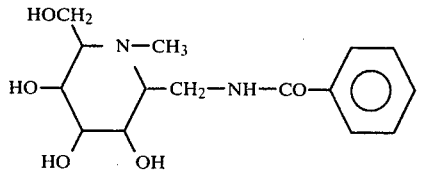

the compound is prepared from 1-benzoylamino-1-desoxynojirimycin according to example 6; m.p. 135°–136° C. (from butanol).

Example 18

1-Tosylaminomethyl-1-desoxynojirimycin

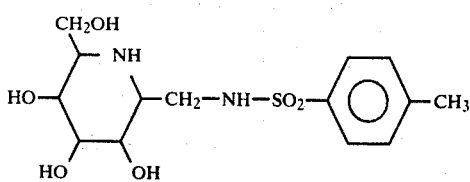

960 mg of 1-aminomethyl-1-desoxynojirimycin are refluxed with 1 g of tosylchloride in 10 ml of methanol/water (1:1) for 3 hours. The solvent was distilled off in vacuo and the residue treated with acetone. The solid is filtered off, dissolved in water and neutralized with a basic ion exchange resin. After removal of the resin the solution is evaporated and residue recrystallized from water. 600 mg 1-tosylaminomethyl-1-desoxynojirimycin of m.p. 173°–175° C. are obtained.

Example 19

N-Methyl-1-tosylaminomethyl-1-desoxynojirimycin

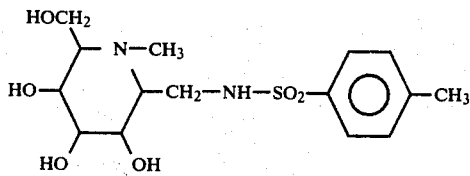

the compound is prepared from the compound of example 18 according to example 6; m.p. 218°–219° C. (from water).

Example 20

1-(N'-Phenylureidomethyl)-1-desoxynojirimycin

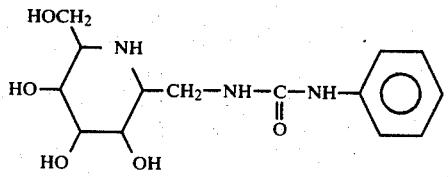

960 mg of 1-aminomethyl-1-desoxynojirimycin are stirred for 15 minutes with 0,8 ml of phenylisocyanate in 10 ml methanol/water (1:1) at −20° C. The mixture is slowly warmed to room temperature and the solvent is distilled off. The residue is discharged onto a column filled with cellulose and the product is eluted with butanol/water (9:1). The fractions containing the product are collected and concentrated. The residue is recrystallized from ethanol and 400 mg of m.p. 161°–162° C. are obtained.

Example 21

N-(1-Desoxynojirimycinyl)-acetic acid-6-lactone

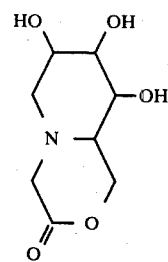

5 g of N-(1-desoxynojirimycinyl)-acetic acid are refluxed in 50 ml of dimethylformamide for 30 minutes. The solvent is removed in high vacuo and the remaining oil crystallized from ethanol. 3.5 g of the compound of m.p. 157°–159° C. are obtained.

Example 22

N-(1-Desoxynojirimycinyl)acetic acid benzylamide

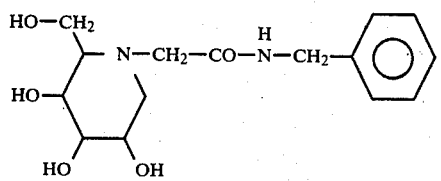

500 mg of the compound of example 21 are refluxed with 1 ml of benzylamine in 20 ml of dimethylformamide for 6 hours. The solvent is removed in high vacuo and the residue recrystallized from ethanol/acetone (1:2). 400 mg of m.p. 129° C. are obtained.

N-(1-Desoxynojirimycinyl)-acetic acid n-butylamide is prepared analogously.

Mass spectrum: The most important peaks in the upper mass range are: m/e=245, m/e=203, m/e=176, m/e=159 and m/e=145.

Example 23

1-Hydroxymethyl-1-desoxynojirimycin

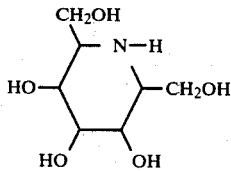

A suspension of 2.3 g of 1-desoxynojirimycin-1-carboxylic acid ethyl ester in 50 ml of abs. tetrahydrofuran (THF) are added to 1.9 g of LiAlH$_4$ in 50 ml of abs. THF. The mixture is stirred for one hour and then refluxed for 5 hours. 20 ml of ethyl acetate, 2 ml of water and 4 ml of 15% strength KOH are added dropwise. The precipitate is filtered off and extracted by a water-methanol mixture. The solvent is distilled off and the residue extracted with methanol. The methanol solution is concentrated and the residue discharged with water onto a column filled with a strongly acidic ion exchange resin (H⊕-form). The column is eluted first with water and then with 0,25% strength aqueous ammonia. The fractions containing the product are collected and freed from the solvent. 500 mg of the compound are obtained.

Mass spectrum: The most important peak in the upper mass range is at m/e 162. Smaller peaks are m/e=144 and m/e 102.

Example 24

6-O-Benzoyl-1-desoxynojirimycin

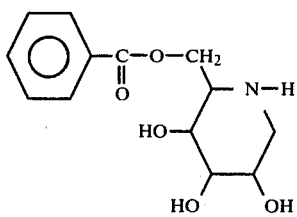

3.5 g of pulverized $K_2CO_3$ and 2.0 g of benzoylchloride are added to 2.1 g of 1-desoxynojirimycin in 40 ml of acetone and 15 ml of water. The mixture is stirred for 3 hours at 40° C. and for 12 hours at room temperature. The salts are filtered off and the solvent is removed in vacuo. The residue is chromatographed on a silica gel column and eluted first with ethylacetate/methanol (10:4) and then with ethylacetate/methanol/water/ammonia (10:4:0.5:0.02). Each 10 ml of eluate were obtained separately and fractions 51 to 57 obtained the desired product (350 mg of m.p. 160° C.).

Example 25

N-(β-Methoxyethyl)-1-desoxynojirimycin

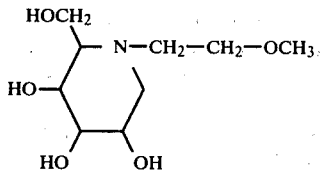

5.2 g o β-methoxyacetaldehyd-dimethylacetal in 15 ml of water and 5 ml of methanol are treated with 0.6 ml of HCl for 48 hours at room temperature and 6 hours at 60° C. Then 1.6 g of 1-deoxynojirimycin and 0.7 g of NaCNBH$_3$ are added at room temperature. The mixture is kept for 12 hours at 50° C. The solvent is removed in vacuo, the residue together with water is discharged onto a column which is filled with a strongly acidic ion exchange resin. The column is eluted first with water and then with 2% strength ammonia. The fractions containing the product are collected and concentrated. The residue is chromatographed on a cellulose-column with butanol/water (9:1). 1.2 g of the compound are obtained with a Rf-value: 0.57 (on thin layer chromatography ready-to-use silica gel 60 plates from Messrs. Merck; running agent: ethyl acetate/methanol/-H$_2$O/25% strength ammonia 100:60:40:2). For comparison Rf-value of 1-desoxynojirimycin: 0.3.

Analogously are obtained N-(β-methylmercaptoethyl)-1-desoxynojirimycin (MS: Most important peaks in the upper mass range are at m/e=220, m/e=206 and m/e=176), N-(β-ethylmercapto-ethyl)-1-desoxynojirimycin (MS: Most important peaks in the upper mass range are at m/e=220 and m/e=176) and N-[β-(β-methoxy)-ethoxyethyl]-n-desoxynojirimycin (MS: Most important peaks in the upper mass range are at m/e=234 and m/e=176.

Example 26

N-n-Nonyl-1-acetaminomethyl-1-desoxy-nojirimycin

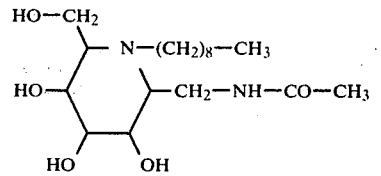

The compound is obtained from 1-acetamino-1-desoxynojirimycin according to example 3.

MS: Most important peaks in the upper mass range are at m/e 329, m/e=288, m/e=270 and m/e 258.

Example 27

1-n-Nonylaminomethyl-1-desoxynojirimycin

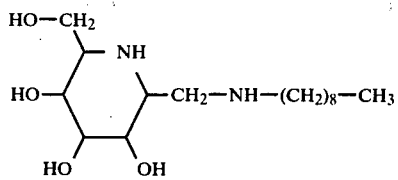

1.2 ml of acetic acid, 1.56 ml of nonylaldehyd and 0.7 g of NaCNBH$_3$ are added to 1.9 g of 1-aminomethyl-1-desoxynojirimycin in 40 ml methanol at 0° C. The mixture is stirred for 1 hour at 0° C. and 12 hours at room temperature. The solvent is distilled off in vacuo and the residue is slurried in water, discharged onto a column filled with a strongly acidic ion exchange resin (H$^\oplus$-form) and eluted first with ethanol/water (1:1), then with 0.3% strength aqueous ammonia and finally with ethanol/0.6% strength aqueous ammonia (1:1). The fractions containing the product are collected and concentrated. 1 g of the compound with Rf-value 0.52 (plate and running agent as in ex. 25) are obtained.

Example 28

N-Methylnojirimycin hydrochloride (a) Preparation of the starting materials 57 ml of chloroformic acid ethylester dissolved in 360 ml of absolute THF are added dropwise to a solution of 294 g of 3-O-benzyl-6-O-triphenylmethyl-1.2-isopropylidene-5-amino-5-desoxy-α-D-glucofuranose in 800 ml of absolute THF and 83.6 ml of triethylamine at 0° C. The mixture is stirred for 2 hours at 20° C., filtered to remove precipitated salt and concentrated. The product is put into ethyl acetate, twice extracted with water, dried and concentrated. 318.6 g of crude 3-O-benzyl-6-O-triphenylmethyl-1.2-O-isopropylidene-5-ethoxycarbonylamino-5-desoxy-α-D-glucofuranose are obtained as a yellow oil.

174.7 g of this oil are dissolved in 340 ml of absolute ether and added dropwise into a suspension of 39 g LiAlH$_4$ in 690 ml of abs. ether at 10° to 15° C. The mixture is refluxed for 5 hours and while cooled with ice treated with 520 ml of ethyl acetate, 40 ml of water and 78.5 15% strength aqueous KOH. The mixture is filtered to be freed from solids, washed with ether and evaporated in vacuo. 144.2 g of 3-O-benzyl-6-O-triphenylmethyl-1.2-iso-propylidene-5-methylamino-5-desoxy-α-D-glucofuranose are obtained as a yellow oil.

This crude product is dissolved in 165 ml of abs. THF and added dropwise at −70° C. into a mixture of 24.6 g of metallic sodium in 820 ml liquid ammonia. Further 2.5 g of sodium is added and the mixture is stirred for 2 hours. Still at −70° C. 91 g of ammonium chloride is added in portions. The mixture is allowed to warm to room temperature within 12 hours. The suspension is stirred into 500 ml of methanol. The solids are filtered off and the filtrate is concentrated. The residue is treated with water/chloroform and the phases are separated. The aqueous phase is concentrated and the crude product is purified by means of a cation exchange resin. After recrystallization from ethyl acetate 14.8 g of 5-methylamino-5-desoxy-1.2-O-iso-propylidene, m.p. 124°–126° C. are obtained.

(b) Preparation of the final product.

A solution of 470 mg of the product obtained according to example 28 (a) in 2 ml of hydrochloric acid is kept at 0° C. for 16 hours. The mixture is concentrated at 20° C. in vacuo and twice dissolved in water and evaporated in vacuo.

The amorphous N-methylnojirimycin-hydrochloride shows a three times stronger effect in the saccharase inhibition test than 1-desoxy-nojirimycin.

Example 29

N-Phenyl-1-desoxynojirimycin (a) Preparation of the starting material 20 g of 1-O-acetyl-2.3-O-isopropylidene-6-p-toluenesulfonyl-α-L-sorbofuranose are heated together with 30 ml of aniline for 5 hours to 110° C. After cooling, 200 ml of ethyl acetate are added and the solids are filtered off. The solution is concentrated in vacuo and excess aniline is removed in high vacuo. The residue is purified by chromatography with a cation exchange resin. After recrystallisation from ethyl acetate/petroleum ether 3.0 g of 6-phenylamino-2.3-O-isopropylidene-6-desoxy-α-L-sorbofuranose, m.p. 156° C. are obtained.

(b) Preparation of the final product 1.0 g of the product obtained according to example 29(a) are dissolved in 4 ml 6 n HCl and kept for 24 hours at 0° C. Then 6 ml water are added and the pH is adjusted to 6–7 with 3 ml triethylamine. 1 g Raney-nickel is added and the product is hydrogenated under a $H_2$-pressure of 3.5 bar. The catalyst is filtered off and the solvent is removed. The product is purified by means of column filled with a cation exchange resin. 470 mg of a slightly yellow oil are obtained.

MS: most important peaks in the upper mass range are at m/e=239, m/e=208 and m/e=148.

Example 30

N-Cyclohexyl-1-desoxynojirimycin

Method A 2 g of 1-desoxynojirimycin are dissolved in 40 ml of abs. methanol and 1.8 ml glacial acetic acid and treated first with 5.2 ml cyclohexane and then with 3.4 g of NaCNBH$_3$. This mixture is refluxed for 96 hours, cooled and concentrated in vacuo. The residue is treated with methanol/water (1:1) and purified by a column filled with a cation exchange resin (H⊕-form). 1.9 g pure product are obtained with a Rf-value of 0.58 (thin layer chromatography 60/F 254 plates of Messrs. Merck, running agent: ethyl acetate/methanol/-water/25% strength aqueous ammonia 120:70:10:1); for comparison: Rf-value of 1-desoxynojirimycin is 0.13.

Method B 1 g of 6-cyclohexylamino-2.3-O-isopropylidene-6-desoxy-α-L-sorbofuranose (prepared according to example 29(a)) is kept for 40 hours in a mixture of 6 ml of methanol/6 n HCl (1:1) at 0° C., treated with 10 ml of water and 3.0 ml of triethylamine and hydrogenated for 2 hours with 3.5 bar $H_2$ and PtO$_2$ as the catalyst. The catalyst is filtered off, the solution evaporated in vacuo and purified by a column filled with cation exchange resing. 610 mg of the compound are obtained, identical with the compound prepared according to method A.

N-Isopropyl-1-desoxynojirimycin (Rf-value=0.45) is prepared analogous to method A.

N-(1-Methyldecyl)-1-desoxynojirimycin (mixture of diastereoimers, Rf-value 0.79 and 0.86) is prepared analogous to method A.

Example 31

1.6-Didesoxynojirimycin (a) 5-Azido-3-O-benzyl-5.6-didesoxy-1.2-O-isopropylidene-α-D-glucofuranose

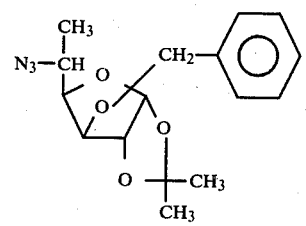

186 g of 3-O-benzyl-6-desoxy-1.2-O-isopropylidene-5-O-methylsulfonyl-β-L-idofuranose, 500 ml of dimethylsufloxide and 65 of NaN$_3$ are heated 5 hours under nitrogen at 120°–125° C. After cooling the mixture is poued into ice-water, extracted three times with petroleum ether, the organic phase washed with water, dried and evaporated. 156 g of crude product is obtained as an oil. 1 H-NMR (100 Mhz, C$_6$D$_6$): δ=7.15 (m 5H), 5.72 (d, J=4 Hz, 1H), 1.32 (s, 3H), 1.17 (d, J=6 Hz, 3H), 1.06 ppm (s, 3H).

(b) 5-Amino-3O-benzyl-5.6-didesoxy-1.2-O-isopropylidene-α-D-glucofuranose

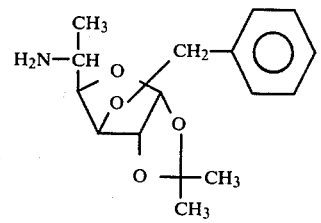

100 g of the crude product of example 31(a) in 200 ml of anhydrous THF are added dropwise to 6 g of LiAlH$_4$ in 250 ml of anhydrous THF. The mixture is stirred for 15 hours and refluxed for 1 hour. While cooling 6 ml of water and 18 ml of 15% strength aqueous KOH are added dropwise. The mixture is stirred for further 15 hours, the precipitate is filtered off and the solvent is removed. The residue is treated with 500 ml of ether and twice extracted with 100 ml of 2 n HCl. The aqueous phase is rendered alkaline by means of 45% strength aqueous NaOH and extracted three times with 200 ml ether. After drying the organic phase the solvent is distilled off and 62.5 g of the compound are obtained as a yellow oil.

1H-NMR (100 MHz, CDCl₃):δ=7.3 (m, 5H), 5.8 (d,J=4 Hz, 1H), 5.70 (d, J=12 Hz, 14), 5.58 (d, J=4 Hz, 1H), 5.42 (d,J=12 Hz, 14), 3.98 (d, J=4 Hz, 1H), 1.45 (s, 3H), 1.30 (s, 3H) 1.15 ppm (d,J=6 Hz, 3H).

(c) 5-Amino-5.6-didesoxy-1.2-O-isopropylidene-α-D-glucofuranose

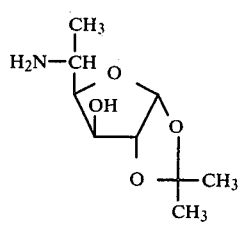

50 g of the compound obtained according to example 31 (b) are hydrogenated in 1 l methanol in the presence of 10 g of Pd on charcoal (5% strength) at 60° C. for 5 hours with a pressure of 70 bar hydrogen. The catalyst is filtered off and the solvent removed in vacuo. 25.7 g of the compound are obtained.

1H-NMR (100 MHz, compound dissolved in CDCl₃ and extracted with D₂O): δ=5.97 (d, J=4 Hz, 1H), 4.50 (d, J=4 Hz, 1H), 4.34 (d, J=4 Hz, 1H), 1.49 (s, 3H), 1.32 (s, 3H), 1.28 ppm (d, J=6 Hz, 3H).

(d) 5-Amino-5.6-didesoxy-D-glucose-1-sulfonic acid

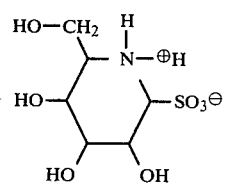

10 g of the compound obtained according to example 31 (c) are suspended in 50 ml of water.

Sulfurdioxide is passed in for 15 hours. A clear solution originates which is warmed up to 60° C. After about 4 hours the compound starts to crystallize. 100 ml of methanol are added and the precipitated product is filtered off after 15 hours. 8.5 g of the compound are obtained, m.p. 180° C. (dec.)

(e) 1.6-Didesoxynojirimycin 10 g of the compound of example 31 (d) are hydrogenated in 120 ml of water in the presence of 13.3 g of Ba (OH)₂.8 H₂O and 10 g of Raney-Nickel for approximately 7 hours. The solids are filtered off and the solvent removed in vacuo. The remaining oil crystallizes after a short time and the compound is recrystallized from methanol to yield 5.3 g with m.p. 163°–164° C.

Example 32

N-(1-Desoxyglucityl)-1-desoxynojirimycin

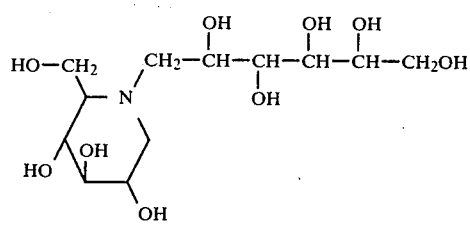

0.8 g of 1-desoxynojirimycin, 7.2 g of glucose, 40 ml of methanol, 10 ml of water, 1.5 ml glacial acetic acid and 1.3 g NaCNBH₃ are stirred together for 15 hours at room temperature. Then the mixture is refluxed for 6 hours, evaporated, treated with 10 ml 2 n HCl, warmed up to 40° C. until the generating of hydrogen ceases, discharged onto a column filled with an acidific ion exchange resin and washed with water. The product is eluted with 0.3 n ammonia, the solvent distilled off in vacuo and the residue chromatographed on 100 g of silica gel (70–230 mesh) with methanol/conc. ammonia (10:5). 1 g of the compound is obtained.

Mass spectrum: m/e=296 (20%), 278 (15%) 176 (100%), 158 (30%), 132 (30%).

Example 33

1-Desoxy-6-O-methylnojirimycin (a) 3-O-Benzyl-1.2-O-isopropylidene-6-O-methyl-β-L-idofuranose

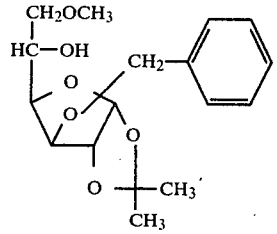

440 g of 5.6-anhydro-3-O-benzyl-1.2-O-isopropylidene-β-L-idofuranose are refluxed in 1.5 l of methanol with 92 g of sodium methylate for 1 hour. After cooling the mixture is neutralized with glacial acetic acid, methanol is distilled off, the residue is discharged on to 300 ml of water and extracted with chloroform. After drying and evaporating 388 g of an oil are obtained.

(b) 3-O-Benzyl-1.2-O-isopropylidene-6-O-methyl-5-O-methylsulfonyl-β-L-idofuranose 384 g of the product of example 33 (a) in 500 ml of pyridine and 760 ml of chloroform are treated dropwise with 148 ml of mesylchloride at 0° C., and the mixture is stirred for 15 hours at room temperature. 200 ml of ice-water are added. The mixture is stirred for 20 minutes and extracted three times with 200 ml of chloroform. The organic phase is washed twice with deluted hydrochloric acid, with water and with 10% strength NaHCO₃-solution and dried. The solvent is removed in vacuo and the residue recrystallized from ethylacetate to yield 347 g to which further 26 g obtained from the mother liquors by filtration over 200 g of silica gel are added. 79% of theory; m.p. 133° C.

(c) 5-Azido-3-O-benzyl-5-desoxy-1.2-O-isopropylidene-6-O-methyl-α-D-glucofuranose

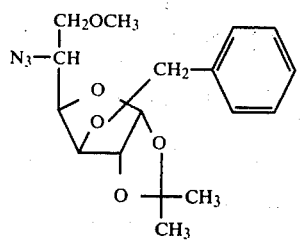

201 g of the product of example 33 (b), 500 ml of hexamethylphosphoric acid triamide and 65 g of sodium azide are heated for 15 hours to 100° to 110° C. under a nitrogen current. After cooling the mixture is poured on to ice-water, extracted four times with ethylether, the ethyl ether phases washed with diluted hydrochloric acid, water and NaHCO$_3$-solution, dried and evaporated in vacuo. 159 g (91% of theory) are obtained as an oil.

(d) 5-Amino-3-O-benzyl-5-desoxy-1.2-O-isopropylidene-6-O-methyl-α-D-glucofuranose 134.5 g of the product of example 33 (c) in 200 ml anhydrous THF are added dropwise to 7.3 g of LiAlH$_4$ in 500 ml of anhydrous THF at room temperature. The mixture is stirred for 4 hours and kept over night. Then 7.3 ml of water are added dropwise, 22 ml 15% strength KOH are added and the mixture is stirred for 8 hours. The precipitate is filtered off, washed with THF and the filtrate is evaporated in vacuo.

The obtained oil is covered with a layer of 300 ml of ethylether and treated under cooling at 0°–10° C. with 150 ml of 5 N hydrochloric acid. The organic phase is separated and washed with hydrochloric acid. The aqueous phases are washed with ethyl ether. The aqueous phase is treated with 100 ml of 40% strength NaOH and extracted three times with 150 ml of ethyl ether. The collected ethyl ether extracts are dried and the solvent is removed in vacuo. 92 g (74% of theory) are obtained as an oil.

(e) 5-Amino-5-desoxy-1.2-O-isopropylidene-6-O-methyl-D-glucofuranose

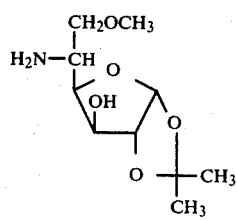

85 g of the product of example 33 (d) in 500 ml of anhydrous THF are added at −70° C. to 1.5 l of liquid ammonia. 30.5 g of sodium in small pieces are added. After 4 hours the mixture is treated with a total of 106 g of NH$_4$Cl in 20 portions and kept over night whereby the ammonia evaporates. The residue is treated with methanol, the precipitate filtered of and the solvent removed in vacuo. The residue is treated with ethyl ether/hydrochloric acid, the ether phase extracted three times with a total of 300 ml of diluted hydrochloric acid and the hydrochloric acid phases collected, treated with 200 ml of concentrated NaOH and extracted three times with a total of 600 ml of chloroform. The solution is dried and the solvent removed. The residue is recrystallized from ethyl acetate to yield 47 g (77% of theory) of the product; m.p. 95°–96° C.

(f) 5-Amino-5-desoxy-6-O-methyl-D-glucose-1-sulfonic acid

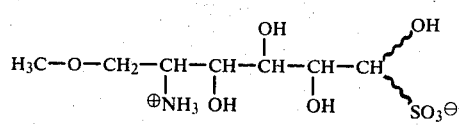

10 g of the product of example 33 (e) are dissolved in 50 ml of water. SO$_2$ is introduced for 2 hours at room temperature and for 15 hours at 60° C. The slurry is treated with methanol, kept for one day, filtered off and dried. 11.8 g (99% of theory) are obtained; m.p. 154° C. (dec.)

(g) 1-Desoxy-6-O-methylnojirimycin

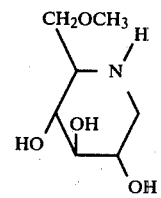

11 g of the product of example 33 (f) in 90 ml of water are treated with 13.3 g of Ba(OH)$_2$.8 H$_2$O. 3 g of Raney-nickel are added and the mixture is hydrogenated for 10 hours. The mixture is filtered and the solvent is removed in vacuo. The residue is treated with 30 ml of 2 N hydrochloric acid, discharged on to a column filled with an acidic ion exchange resin and washed with water. The product is eluted with 0.3 N ammonia and obtained after evaporating in vacuo. After recrystallization from ethanol 5.5 g (78% of theory) of m.p. 145° to 146° C. are obtained.

What is claimed is:

1. An animal feedstuff or premix thereof which contains an amount effective for increasing the proportion of lean meat to undesired fat of an active compound of the formula

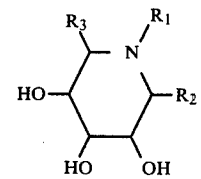

in which
R$_1$ is C$_1$–C$_{30}$ alkyl, C$_2$–C$_{18}$ L alkenyl, C$_2$–C$_{18}$ alkinyl, C$_3$–C$_8$ cycloalkyl, C$_3$–C$_8$ cycloalkenyl, C$_3$–C$_8$-cycloalkinyl or phenyl (a), said alkyl, cycloalkyl, cycloalkenyl and cycloalkinyl being unsubstituted or substituted by hydroxy, C$_1$–C$_4$-alkoxy, acyloxy, amino, mono-C$_1$–C$_4$ alkylamino, di-C$_1$–C$_4$ alkylamino, acylamino, mercapto, C$_1$–C$_4$ alkylthio, halogen, C$_1$–C$_4$ alkylcarbonyl, carboxyl, nitro, cyano, formyl, sulfo, naphthyl or phenyl (b); said acyl being derived from an aliphatic carbocyclic acid having from 1 to 7 C-atoms, a phenyl carboxylic acid, unsubstituted or substituted by carboxy, hydroxy, halogen, C$_1$ to C$_4$ alkyl, C$_1$–C$_4$ alkoxy, nitro or amino; said phenyl (a) being unsubstituted or substituted by $C_1$ to $C_{10}$ alkyl, $C_1$ to $C_{10}$ chloroalkyl, $C_1$ to $C_{10}$ nitroalkyl, $C_1$ to $C_{10}$ cyanoalkyl, $C_1$ to $C_{10}$ alkenyl, hydroxyl, $C_1$ to $C_4$ alkoxy, amino, mono-$C_1$ to $C_4$ alkylamino, di-$C_1$-$C_4$ alkylamino, mercapto, $C_1$-$C_4$ alkylthio, carboxyl, $C_1$-$C_4$ carbalkoxy, sulfo, $C_1$-$C_4$ alkylsulfonyl, phenylsulfonyl, aminosulfonyl, $C_1$-$C_4$ alkylaminosulfonyl, di-$C_1$-$C_4$ alkylaminosulfonyl, nitro, cyano, formyl, $C_1$-$C_4$ alkylcarbonylamino, $C_1$-$C_4$ alkylcarbonyl, benzoyl, benzylcarbonyl or phenylacylcarbonyl;

said naphthyl and phenyl (b) being unsubstituted or substituted by hydroxyl, amino, $C_1$-$C_4$ alkylamino, di-$C_1$-$C_4$ alkylamino, $C_1$-$C_4$ alkoxy, nitro, cyano, carboxy, $C_1$-$C_4$ alkoxycarbonyl, $C_1$-$C_6$ alkyl, halogen, $C_1$-$C_4$ alkylthio, mercapto, $C_1$-$C_4$ alkylsulfonyl, sulfoaminosulfonyl or $C_1$-$C_4$ alkylaminosulfonyl $R_2$ is —H, —OH, —$SO_3H$, —CN, —$CH_2NH_2$, —$CH_2NH$— ($C_1$ to $C_{14}$-alkyl),

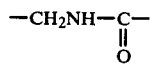

($C_1$ to $C_{14}$-alkyl), —$CH_2$—NH—$SO_2$— ($C_1$ to $C_{14}$) alkyl, —$CH_2$—NH—$SO_2$-phenyl,

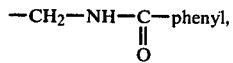

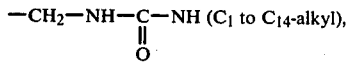

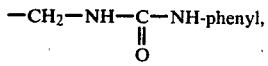

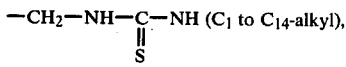

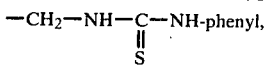

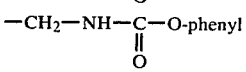

—$CH_2$—NH—C(=O)—O-phenyl wherein phenyl is unsubstituted or substituted by methyl, ethyl, methoxy, or nitro, $R_3$ is —H, —$CH_3$, —$CH_2OH$, —$CH_2$—$NH_2$, $NHR'$—$CH_2$—, $NR'R''$—$CH_2$—, $R'CONH$—$CH_2$ $R'CO$—$NR''CH_2$—, $R'O$—$CH_2$—, $R'COOCH_2$—, $R'SO_2NHCH_2$—, $R'SO_2$—$NR''CH_2$—, $R'NH$—$CO$—$NH$—$CH_2$—, $R'NHCS$—$NH$—$CH_2$—, $R'O$—$CO$—$NH$—$CH_2$—, wherein $R'$ and $R''$ are the same or different and each has the meaning hydrogen or any of the meanings given above for $R_1$, in admixture with an edible non-toxic feed carrier.

2. An animal feedstuff or premix thereof of claim 1 in which the active compound has the steric formula

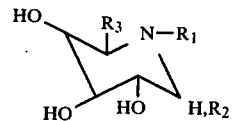

wherein $R_1$, $R_2$ and $R_3$ have the same meaning as defined hereinbefore in claim 1.

3. An animal feedstuff or premix thereof of claim 1 in which the active compound is N-($\beta$-hydroxy-ethyl)-1-desoxynojirimycin.

* * * * *